United States Patent
Ryan

(10) Patent No.: US 7,273,718 B1
(45) Date of Patent: Sep. 25, 2007

(54) ISOLATED GENOMIC POLYNUCLEOTIDE FRAGMENTS FROM CHROMOSOME 10Q25.3 THAT ENCODE HUMAN SOLUBLE AMINOPEPTIDASE P

(75) Inventor: James W. Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 481 days.

(21) Appl. No.: 10/457,715

(22) Filed: Jun. 9, 2003

Related U.S. Application Data

(60) Provisional application No. 60/386,941, filed on Jun. 7, 2002.

(51) Int. Cl.
- *C12N 15/11* (2006.01)
- *C12N 15/17* (2006.01)
- *C12N 15/79* (2006.01)
- *C12Q 1/68* (2006.01)

(52) U.S. Cl. ........................ 435/23.1; 435/6; 435/69.1; 435/252.3; 435/320.1; 977/704

(58) Field of Classification Search ............... None
See application file for complete search history.

(56) References Cited

U.S. PATENT DOCUMENTS 6,399,349 B1 * 6/2002 Ryan et al. ............... 435/226
6,812,339 B1 * 11/2004 Venter et al. ............. 536/24.31
2004/0265849 A1 * 12/2004 Cargill et al. ............... 435/6

OTHER PUBLICATIONS

Printed alignment of the nucleotide sequences of SEQ ID No. 13,390 of US Patent No. 6,399,349 and SEQ ID No. 2 of this application.*

Sprinkle, T.J., et al., 1998, "Assignemtn of the membrane-bound human aminopeptidase P gene (XPNPEP2) to chromosome Xq25", Genomics, vol. 50, pp. 114-116.*

Cottrell, G.S., et al., 2000, "Cloning, expression, and characterization of human cytosolic aminopeptidase P: a single Manganese(II)-dependent enzyme", Biochemistry, vol. 39, pp. 15121-15128.*

Sprinkle, T.J., et al., 2000, "Cloning, chromosomal sublocalization of the human soluble aminopeptidase P Gene (XPNPEP1) to 10q25.3 . . . ", Archives of Biochemistry and Biophysics, vol. 387, No. 1, pp. 51-56.*

* cited by examiner

*Primary Examiner*—Kathleen Kerr Bragdon
*Assistant Examiner*—William W. Moore
(74) *Attorney, Agent, or Firm*—Cheryl H. Agris; The Law Offices of Cheryl H. Agris

(57) ABSTRACT

The invention is directed to an isolated genomic polynucleotide fragment that encodes human soluble (cytosolic) aminopeptidase P, vectors and hosts containing the fragment and fragments hybridizing to noncoding regions as well as antisense oligonucleotides to these fragments. The invention is further directed to methods of using these fragments to obtain human soluble aminopeptidase P and to diagnose, treat, prevent and/or ameliorate a pathological disorder.

21 Claims, No Drawings

SEQUENCE LISTING

<160> NUMBER OF SEQ ID NOS: 2

<210> SEQ ID NO 1
<211> LENGTH: 623
<212> TYPE: PRT
<213> ORGANISM: Homo sapiens

<400> SEQUENCE: 1

```
Met Pro Pro Lys Val Thr Ser Glu Leu Leu Arg Gln Leu Arg Gln Ala
1               5                   10                  15

Met Arg Asn Ser Glu Tyr Val Thr Glu Pro Ile Gln Ala Tyr Ile Ile
            20                  25                  30

Pro Ser Gly Asp Ala His Gln Ser Glu Tyr Ile Ala Pro Cys Asp Cys
        35                  40                  45

Arg Arg Ala Phe Val Ser Gly Phe Asp Gly Ser Ala Gly Thr Ala Ile
    50                  55                  60

Ile Thr Glu Glu His Ala Ala Met Trp Thr Asp Gly Arg Tyr Phe Leu
65                  70                  75                  80

Gln Ala Ala Lys Gln Met Asp Ser Asn Trp Thr Leu Met Lys Met Gly
                85                  90                  95

Leu Lys Asp Thr Pro Thr Gln Glu Asp Trp Leu Val Ser Val Leu Pro
            100                 105                 110
```

-continued

```
Glu Gly Ser Arg Val Gly Val Asp Pro Leu Ile Ile Pro Thr Asp Tyr
    115                 120                 125
Trp Lys Lys Met Ala Lys Val Leu Arg Ser Ala Gly His His Leu Ile
    130                 135                 140
Pro Val Lys Glu Asn Leu Val Asp Lys Ile Trp Thr Asp Arg Pro Glu
145                 150                 155                 160
Arg Pro Cys Lys Pro Leu Leu Thr Leu Gly Leu Asp Tyr Thr Gly Ile
                165                 170                 175
Ser Trp Lys Asp Lys Val Ala Asp Leu Arg Leu Lys Met Ala Glu Arg
            180                 185                 190
Asn Val Met Trp Phe Val Val Thr Ala Leu Asp Glu Ile Ala Trp Leu
        195                 200                 205
Phe Asn Leu Arg Gly Ser Asp Val Glu His Asn Pro Val Phe Phe Ser
    210                 215                 220
Tyr Ala Ile Ile Gly Leu Glu Thr Ile Met Leu Phe Ile Asp Gly Asp
225                 230                 235                 240
Arg Ile Asp Ala Pro Ser Val Lys Glu His Leu Leu Leu Asp Leu Gly
                245                 250                 255
Leu Glu Ala Glu Tyr Arg Ile Gln Val His Pro Tyr Lys Ser Ile Leu
            260                 265                 270
Ser Glu Leu Lys Ala Leu Cys Ala Asp Leu Ser Pro Arg Glu Lys Val
        275                 280                 285
Trp Val Ser Asp Lys Ala Ser Tyr Ala Val Ser Glu Thr Ile Pro Lys
    290                 295                 300
Asp His Arg Cys Cys Met Pro Tyr Thr Pro Ile Cys Ile Ala Lys Ala
305                 310                 315                 320
Val Lys Asn Ser Ala Glu Ser Glu Gly Met Arg Pro Ala His Ile Lys
                325                 330                 335
Asp Ala Val Ala Leu Cys Glu Leu Phe Asn Trp Leu Glu Lys Glu Val
            340                 345                 350
Pro Lys Gly Gly Val Thr Glu Ile Ser Ala Ala Asp Lys Ala Glu Glu
        355                 360                 365
Phe Arg Arg Gln Gln Ala Asp Phe Val Asp Leu Ser Phe Pro Thr Ile
    370                 375                 380
Ser Ser Thr Gly Pro Asn Gly Ala Ile Ile His Tyr Ala Pro Val Pro
385                 390                 395                 400
Glu Thr Asn Arg Thr Leu Ser Leu Asp Glu Val Tyr Leu Ile Asp Ser
                405                 410                 415
Gly Ala Gln Tyr Lys Asp Gly Thr Thr Asp Val Thr Arg Thr Met His
            420                 425                 430
Phe Gly Thr Pro Thr Ala Tyr Glu Lys Glu Cys Phe Thr Tyr Val Leu
        435                 440                 445
Lys Gly His Ile Ala Val Ser Ala Ala Val Phe Pro Thr Gly Thr Lys
    450                 455                 460
Gly His Leu Leu Asp Ser Phe Ala Arg Ser Ala Leu Trp Asp Ser Gly
465                 470                 475                 480
Leu Asp Tyr Leu His Gly Thr His Gly Val Gly Ser Phe Leu Asn
                485                 490                 495
Val His Glu Gly Pro Cys Gly Ile Ser Tyr Lys Thr Phe Ser Asp Glu
            500                 505                 510
Pro Leu Glu Ala Gly Met Ile Val Thr Asp Glu Pro Gly Tyr Tyr Glu
        515                 520                 525
```

```
Asp Gly Ala Phe Gly Ile Arg Ile Glu Asn Val Val Leu Val Val Pro
        530                 535                 540
Val Lys Thr Lys Tyr Asn Phe Asn Asn Arg Gly Ser Leu Thr Phe Glu
545                 550                 555                 560
Pro Leu Thr Leu Val Pro Ile Gln Thr Lys Met Ile Asp Val Asp Ser
                565                 570                 575
Leu Thr Asp Lys Glu Cys Asp Trp Leu Asn Asn Tyr His Leu Thr Cys
            580                 585                 590
Arg Asp Val Ile Gly Lys Glu Leu Gln Lys Gln Gly Arg Gln Glu Ala
        595                 600                 605
Leu Glu Trp Leu Ile Arg Glu Thr Gln Pro Ile Ser Lys Gln His
    610                 615                 620
```

<210> SEQ ID NO 2
<211> LENGTH: 58735
<212> TYPE: DNA
<213> ORGANISM: Homo sapiens

<400> SEQUENCE: 2

```
cagagctggc actcagccca tctttattaa atgaactctc cctacattcc tgcctacagt      60
catgagctgg gtacaatggc ctctgagagg acactgagtg gcagccacat gagcgcctcc     120
aggtcagtag gaaacctcga gagggtcctc cccgtgtcat ccttctctat aataatccat     180
ccgcttcctc agctggctgg ccgtctccac tctctccaca gatccacact gccatctgct     240
ggcagaaggc acaggagcat ctcaacgccg ctgtgcccgc cttgcagggc gtgcagcaat     300
tcccaatgcc tgatgcccag agtaatgccc tcctaaccct tggcatgtga cagtgtcagc     360
cgtagaaact tcaggctctg ttccttgtga cttcccaagc atctccctgt actcatcctc     420
cctttcttca caaattgttc tctagttcag aaacgtgtct tcctccacca tcccacctgg     480
gcatactgca gactcctttg accctgggtt agagaaaaga gagcacagaa gagagccaga     540
caccttccac ttcgcagctc agcccttctc taaggcactt cactacagat catgatgccc     600
gagcaggctt ggttagattt tctatagtga gatctgtgat ttgtttgttt cacatttcaa     660
caactcagaa atgaggatgc atcttagagt catgaggtct cgtgtgaaaa ctttgacacc     720
ttctggagag atcaagaagc acgagcatta acgtgtctca cttttaaatag gtgaagtgca     780
tgatgtgtga attatatctc aataaggcta cacttagttt tgtttaaagc tgtctcaggt     840
tgggttgggg aacatggatg tatacacaaa gctaacattc aaggatacac tctacaggag     900
ctttctcttt ccatcctcat agcctaatga ggagacatcg ccgctaacct cacattacag     960
agcaggaaat gggggctcag agaggctgtg ctcttgccca gggactcaca gctggtacac    1020
agtgccatct gctttagaac ccatgttcta aaccactata tactcttctt tcacatgtta    1080
cttctataaa ggaaaaataa agaaaaaatt tctgttgtaa gacaacaaac tttcttttt     1140
gatttaaaaa aaaaaaagtt atggtaggaa gtatccaaga tgtcctccaa taggtgaatg    1200
tataaacaaa ccttgtgtat ctgtaacaag aacattattc catgataaaa agaaataagc    1260
taacaagcca tgaaaggaca tggatgaacc tgaaatacat attgctaagt gacagaagcc    1320
agcatgaaaa attctacatg ctgtttgatt cctattatat ggtatctgga aaaagcaaaa    1380
ctatagagac agtaaaaaaa aaaaaaaaa aaaaaaatca ctggttgcca ggaccttacg    1440
gggaaatagg aggttgaaat cagggaagcc caggggatat ttttttcagg tggtgaaact    1500
attctgtatg attgtgtaat tgtggataca tgacactatg catttatcaa acatactga     1560
accttacagc acacagagtg aaccataatg tatgcaaatt gaaaaaaaaa aaccatttag    1620
```

```
gaggtcaaag gaatcccagg atggaatgca gtatgtgata aaatgatcta actatattaa    1680
aatgtatgaa actgtaatac cttactgaaa gaaggggagg gggtgagaag gaaggtgctg    1740
acctaagcaa ctttggaaat aaatgagtgg agtctgtaaa accgaagcaa aaataattgc    1800
atataaacac tatactcggc cgggtgtggt ggctcatgcc tgtaatccca gcattttggg    1860
aggccgaggc aggcggatca cgaggtcagc agaacgagac catcctggct aacagggtga    1920
aaccccatct ctactaaaaa atacaaaaaa ttagccaggc gtggtggctg cacctgtag    1980 taccagctac tcgggaggct gaggcaggag aacggcgtga acccgggagg cggagcttgc    2040
agtgagcgga gatggcgcca ctgcactcca gcctgggcga cagagcaaga ttccgtctaa    2100
aaaaaaaaaa aaaccaccgt actcaagttg ataaagctgt tccccacagt atacaggtta    2160
gcaatcttaa cactgctaca catgtacact agaattaagc aattaagtga aatataagtg    2220
aaatggatgg cggatggtgg gagccaagtt ctcactgatg aagtaggaag tcacagagaa    2280
gcaaggggag atgatcatga attagagttg gagacatcag tgtgaactca tgtttagttt    2340
aatatagaaa cagatggtta catatagaaa cactgaaaga tagttgtgtg tgtatatata    2400
tatatacata tacatatgca tacctctttg tccttgctct cagctgagac ggcctagcag    2460
caaggacaag ccagtaagag aacctatcta gtgctcagat cttggttttat tttatttatt    2520 tatttattta tgagatggag tttcactctt gtcatccagg ctgaagtgca gtggcatgat    2580
cttggttcac tgcaacctcc acttcctggg ttcaagtgat tctccagcct cagcctcccg    2640
agtagctggg attacaggtg cccaccacca ggcccagcta attttttgtat ttttagtaga    2700 gacaaggtgt aattttttgta ttttttagtac agacagggtt ttgccatgtt ggccaggctg    2760
gtctcgaact cctgacccca ggtgatctgc ccgcctcggc ctcctaaaact gctgggatta    2820 cagttgtgag ccaccatgcc cagcctggat cttggttttta aataccttttc tccggtaaaa    2880 ggcactagag cttcttaaag aaatgattga ttctagaatt ggagcaggaa atacacaaga    2940
tgagcctgga gcaatttgta gtgccagaaa gtaaagaagt gcttacaaca cacacacaca    3000
cacacacaca cacacacaca cacacgatgg gatatatcaa aggaacacag gagacagctg    3060
aaagagccct cagtggccaa agctggaaca atttaaagaa agcagtattg attataatcc    3120
aaagtataaa ataaatatct gcaagcctat acaaatatga aaaataaaa gaatgtggaa    3180 aaagagacaa atctgtgcag aagcattcta ataatttac atatattctg tgccctcaag    3240
aaagttgaac ataacttcca ctccttaagt atgggctaca cgtagtgact ttccaagaat    3300
acaggataag caggggggttg aaagagtcac tttcctatgg agaaatatga caaacactgc    3360
ctcagccaga tgatcaaggt taacctcatc agtcaaaagc catgttgata gtatgtaccc    3420
ttgacatgat gtgacaaaaa tggcactttta cctccatcga cttccgccta taaaactaaa    3480
accacagtct aatcatgaga aaatatttta aaatcccaat ataaggatat tccacaaaat    3540
atttgaccag tattcctcaa aactgtccag gtcatcaaaa atgaagaaaa tctaagaaac    3600
tgtcacagcc taagaagaca ggacaactaa atataatgag ggactccgga tgggattctg    3660
gaagagaaaa aggacattag ctaaaaacta gggaaatctg aataaagtgc agcctttagt    3720
tactaatact gcgataacat tggttcgtta attgtgacag atgtactata ctaagatctg    3780
aataatagtg aaaactaggt gtggagcata agaaactct ctgtactttc ttcgcagtaa    3840
atctaaaact gttctaaata ataaagtttt tttttaaaaa taatgatata ggaaatttgg    3900
gaggtatttg ggaaggaaga aataagggac aataaataga gaattcaaaa cagaattgca    3960
```

-continued

```
catctccttc ttgttTaaaa atataggtgc cctgtcacga taaacaacta acatttactg    4020
agagctgatt acatgcctga cagcatgcta agtgatttgt gcatattatt tcttttaatc    4080
ctcacaaata tgctgtcaga atataccatc accctcattt tgtaaaggat gaaactggag    4140
gtcagagaag atacataatt tacccaacca aggtcaccag ctaggaagta atgggactga    4200
attcaattct gctcccatca tccattctgt tgtaaacttg tttggaatgt cttcatcaat    4260
tcttaaatgt atccatcaat aaatatttat tgagtagctc ttatgtgcct ggtcctgagc    4320
aatagctggg gctgggcccc aaggaactac aagtctagtt ggagagacat gggaaaggtt    4380
aaatttcata aagagaaagt caattacagt ttgtgaagaa aatgaatgcc agcaaaactt    4440
agagcaagga cttgtagctg aataattgg gaaacacttc atgaagaagc tatgtgggaa    4500
ttgcactaga ttctaaagat gggaaggaat tcaaagttga aggacaggag gaagccctcc    4560
aggaagaaag gctggagcca atgactgtac ctatctgcct gcagaatagg tgttaaggaa    4620
gtagcgcaat ccacctggtg caaacagccc tggcctgaga gccaggagac cagaaattga    4680
tgtgaagttg gtcttagcct tcaatctgga cctcatatgg ttcactcttt ttttgttatt    4740
gttgttgttg ttgtttgtcg agatggagtc ttgctctatc acccaggctg gagtacagtg    4800
gcgagatctg ggctcactgc aacctccacc tcccaggttc aagcaattct cctgcctcag    4860
cctcccgagt agctgggatt acaggcttgt gccaccatgc ccagctgatt tttgtaattt    4920
tttttagtag agactgggtt tcgccatgtt ggccagtcta gtttcaaact cctgaccttg    4980
tgatctgcct acctcagcct cccaaagtgc tgggattaca atcatgagcc accatacccg    5040
gcccttccaa cactctttaa aaaaaaaag aagaaaaaa ggatgtttag aatccaccct    5100
aacaattaga atacagagca ttctggactg agaaagagat aagaacatta gctaggtgca    5160
cacctgtaat cccagctact tgggaggctg aagaggaagg attgcgtgag cccaggagtt    5220
tgaggttaca gtgagctatg attgtgccac tgcactccaa cctggacaac agagtgagac    5280
cctctctgta aataagtaag aaagagatcc ccaaccaaat gacctagctt gtcttttgca    5340
gcttctactt tcagagtgtg cagcggggaa cgcttaagcc tcaggtgtct gtgatgctgc    5400
tcagccgcca acctttccct ggcctccagg ctgccaggaa ggggatcctg gctgggtacc    5460
tgtccttaca gagcttgcag tgcagtaaga agccacagct tctgcccgag aaccaatttt    5520
agatcacaca tgtgttttgt tagacctaca tgagattttg ttttagtttg taaaatgtta    5580
cattggttgt aaatgtttaa aaactaggat atgcccacat acacagtttc agctcctctt    5640
taaaatcctg tttcaggcca gatgtgatgg ctcacgccta taatgccagc acttagggag    5700
acagaggcgg taggatacta ccttgagccc aggagttaga cacctgcctg gcagcatag    5760 caagaccatg ttctccacaa aaagtaaaaa agacataaaa atagtaaaat cacatcttca    5820
ctctgcccct gtgagctctc tttatcccaa ggcagacagg ctggagatgg gacttcctgc    5880
cacctttaca tagagtactg ctctcccatc catcataggc taatcctacc agctctaact    5940
cattcccttg cccacctggc cactgttggc actgtttctt tttaaatttt ggggtttgtt    6000
tattattgta ctttaagttc tggtatgcat gtgcagaaca tgcaggtttg ttacataagt    6060
acacatgtgc catggtggtt tgctgcactc atcaacccat catccaggtc ttgagccccg    6120
catgcattag ggatttgtcc ttatggtttc cctcccttg ccccccaccc ccgacaggc    6180 cccagtgtgt gatgttcccc tccctgtgtc catgtgttct cattgttcaa ctcctacttg    6240
tgagtgagaa cacgagatgt ttggttttct gttcctgtgt tagtttgctg agaatgatgg    6300
tttccagctt catccatgtc cctgcaaagg acatgaactc attctttta atggctgcat    6360
```

```
agtattccat ggtgtatatg tgccacattt tctttatcca ctctatcatt gatcggcatt      6420
tgggttggtt ccaagtcttt gctattgtaa atagtgccac aataaacata cgtgtgcatg      6480
tgtctttata gaatgatttg taatcctttg ggtatatacc cagtaatggg attgctgggt      6540
taaactttgt tattaaactt aacacagatg caaaacacca tgtaaagcaa acatggggct      6600
tattgaatta cataatgagc acccttgtca ctacaactaa tgtcatttta ttttcttctg      6660
gcctaaactg ttgctttgaa aatttctgat ggcaatataa ttttttttc accataagtt      6720 acttggtctt ttgtctgatt aaccaggaaa ttttttttag gtacagtaat tctaccataa      6780
gtatgccctg ttggctattc taggtttatt tattgagtta tacggcatgc ctcttcaaag      6840
tgtagtttcg aacttttttt tatctcagga gtgttttctt atagtttttt atatttgttc      6900
tgttcccttt agctttcttc tttgttgaaa cctattatgt aaatgttgaa tgttgttgcc      6960
tatcttctat atttctttca cttaaataat tttattcat tttggtttca attctccttt      7020
tagtcatctc ctgtttatct taagacatta tctgtggtgt ttattcattc ctgtgttcct      7080
cctactttag tcttcattat ttcaattgat tttttttctca ttctttcctg agttctctca      7140
cttaattcct cagcttctct aattctctgt tgtatattgt ttttgcatac actgttttta      7200
aacctgtaaa tgtgctttga acattacaga ttttcatctg tttatgggca tgtctctgtg      7260
atgtgtttca ttgtaggcac gtcattctgc accttatttt cctttctaag tttacatagc      7320
attttacctc aacctttttt tctgtttctt atttttatgt gaaattttc tgaacttctg      7380 ggagacttta gaatagtttt tttcttattt agggctctag agctcccttt tctgttgatt      7440
tcctgaagta ttcaaaaata tagcacttac ttttggagat ctcctggctc tgttcccctc      7500
caaaagaacc ttctttctcc tttgcctccg ctgtacctgt cctgctcctc tttggctcct      7560
atccctcagc gtggggcttg gtcgtgggag ttcctgggac gctgactgct ccagcccctg      7620
tgggccttac caaaaacctc tcatactcac ccactggagg tgcaaactgc tcccagtgtt      7680
agtggctgtt ctcagattgg ctccgtgaga ttctgagctc ctgatggcta ttgtggggtt      7740
ctgttctcag gtccatcaga taccccatca cttccttcag cttcctcctg cacagatgct      7800
gataatacgc tggttagtct tcacgtgctc ttattaaggg tttgtggaga tgcttgacac      7860
ctgtatattt ggtgcaaagc tcatccctga attttagttt tgctacccca gtttatccgt      7920
gtttttatga agttatttgg agagattcaa acactatggc acaactgctg ccaccttgcc      7980
aggatctgca tcgttgttct taatccatga ttctatgaat ttcttaactg ctgcaccagc      8040
tacctgcagg aactagcaag cacagtatcc ttcctcccct ctcgcagccc tcccagtccc      8100
ccatcttgtc tcttgctaga ggccaacggt gcttgaaaga tgccccaaag cactctactt      8160
tgtcttcata tcattactgg tataaacccc cagttgctgg gaaacacgag ggcaacacct      8220
ccctcatggc ttgttagttc aaccttggtt cctttcacaa ttgcccaccc ctaaccggga      8280
atgagcctga tgaggaacaa ctgatggtta ctgtcaggca gccagatgcc aggcacagcc      8340
ctcaagctaa agaagtggtg agagctgggg tggtgggggc agcccctca ctggcaggag      8400 gcacagatgg actctttcca gaaggcgaac aagcgtccca caagtcagtc cctggagtgt      8460
tcacagcagg ggccccacat ctgtcccctt ccttgaatcc tcctacctta tacataaaac      8520
ttcaccaggg aatacagtga gcaagacaaa gaaacgagat cagcttcctt ctttaaattc      8580
aacacaatgc ccattttcct acccaacatt tatttttatca tttatttaaa agtgaggaag      8640
agtgattttt tttttttta tctacatttt tatctcctca tcttccctct gagctctggc      8700
```

```
acattagagt tttattctgg tcctcaatcc ttatggggcc atcttgccta gtttatgtct   8760
cttggactta atgccaagac aaagcaggtc caggcaggaa gctccaagca cccagcacct   8820
gttacctttg cttctcgggc tacagccaat taaatcaaac tttgctctga ggctgccttg   8880
gggaagaaca ggtttaacag cctgatgaac agacagtgga gttgccgtca cacttgagtt   8940
acgactattt caactccaaa tcaactgcga ttcatgcctc ccatttcctc agcaagagaa   9000
gactttggga tatcagagaa gacaacagcc tgagtcctaa gggaaatctt ctaacttcca   9060
gaggaatgac agatgagaaa catgcttaat acattctatc atttggggag aaatttctct   9120
tttaagtcca atgttatggt acatattaga aatatgacca agcatggaca aaaggcattc   9180
aagaattgat ctttgatgga tcaaaatatg tcctattatt gggaggcact gcttctatgc   9240
tttcctgacc tcgttagaaa tataccgaga ggcagcagtg aatcttgctt cctcccacat   9300
agcacattga aatcaatgat ccttgagaga aaaaaaaaaa aaaaaagag gagggtggga   9360
gacgaaaagc aaacaaatgc tggttcattt gttttaggc actctatgta ggaccaccct   9420
ggttctgaat ggtaaatata gattgtttca tttcattttc tgctccgcca ggtggagaaa   9480
gtaatgggca cttacagcca tgctttggta aatggccaaa gtatgcttat atttattcat   9540
ttgtcaaagc cattcgaatt aaatatatgg tttaggattt aaggagagga ttctgggaag   9600
atggtaggaa gcactcggaa agtgtctctc cacctagaca caattgcac tggcagaatc    9660
tgcctgatgt aactacttta gaactctgga gtctactgaa cgcttgcaac ttccagagga   9720
caacttggat ggtaaatgaa cgttaatttc aatccatttc agctcttagc acagtagcag   9780
ctaccaatgt ctactcctaa ccccttggca ggaacttatg cacacgttcc cagagcaact   9840
ggcatacagc ttgtgggagc caaaatgaac aaaaggaaac ttgccctcca aatactgcag   9900
acctgtgttc tggtaactgc ttctgaacac agagacgcag acaaagaggt gggcagccac   9960
tgttgctgta catcccatcc cccgactgtt agaagtccct tctcccttc tggctgaagt   10020
gacttccaga ggatttaaag gaccagtacc cttttcctgc ccttcatttt tcttttttccc  10080
tcgttgggag ccagacatta agtaatagga cattcaaaaa caactgcaca tagggggaa    10140
attagagact gactgcacat atccagggaa aggctcaagc tcagaaaaaa acctgagaag  10200
accttaagtt gatacctcag gctgatactt ggcccagaga ctatctacaa caataaataa  10260
taataataat aacacacatt aacaaaaaag ggcaaaccct agggaaagag gaaaatctga  10320
tttccagagt tgccacatta ttagattcaa atgtccaatt gtcaaccaaa actcacaagg  10380
catacaaaga aacaggaaag tatggcccat tcagaggaaa agaaaaatcc acagaaaaaa  10440
aggaaatatc aatagagaca gacaacataa aaagaaacca aaatgaaatt ctggagctga  10500
aaagtacagt aactgaaatg aaaaattcac cagagggatt caaagcacat atgagcaggc  10560
aaaagagaaa atcagtgaac ttgaagatag gataacagaa attttgagtc tgaaaaacag  10620
aaaaaatatt aaagggaaca gagcctagaa gacctgtggg acaccatcaa gctgaccaaa  10680
atatacattg ttagagtccc aggagaaggc agaaagcagc agagagaata tctgaagaaa  10740
taatggctgt ataattccca aatctggtaa aagacatgaa tgtaaacatc caagaaaccc  10800
aataaaccac aagtaagatt aactccaaga gatacacaca aaaatacatt atagtcgagc  10860
ttccaaaagt caaaaacaga gagaatcttg aaagcagtga gagaaaagct acttaccacg  10920
taaaagggat cttcagtgag attacctgca gatttctcat cagaaattct ggaggccaga  10980
aggcagtggg ccaatattca aaatgttaaa agaaaaaaaa aaaaactgac aaccaaagaa  11040
tcctatatcc agcaaaactg cccttcaaaa gtgagggaga aattaagagg ttcccaggta  11100
```

-continued

```
aacataagct gagggagttc agtaccacta gacccaccct gcaagaaatg cttataggag     11160
ttctgcaaag tacaatgaaa ggacactaga cagtaaccca aagcagtatg aagaaataaa     11220
gatctcaaga aaaataaata cattgggcaa ttataaaaac cagtattagt gtactgatag     11280
cttgtgattc cagtttttgt tttctatatg atttaagact aatacatttt ttaaaaaatt     11340
atgtctaaat gctagtatta ctgtttttaa aaagttaatg aggctagttt taaaacaata     11400
taaccatacg atggaattaa gtcattaaaa ataattcaat ctaaatatt gccaagttaa      11460 aagataaaat tgtatacgta cagaataatt cactgtttgt aaatgtgata tgttcatata     11520
tggcatattc tttcatacat acacaaataa tcagtatttt agtaaatttt gaatacaaaa     11580
aaaaaggagt cagcaaaaat ataaagcaga taatagtggt tatatctaag gagtatgtca     11640
ggttggatta ataaaaaagc agaccctaaa acaaggattt gcatgtaaat ggttcattca     11700
ggatggtacc aggaaacact aatgggacag gaagaaagta ggacatggaa gagaagaaag     11760
aaaacaaagg gttggttatt gagcaagtta ccatggtggg caagtggggc tcaatcccac     11820
tgggaaaccc tgagtgacaa tgtaagacat acctctgata tcttagccaa aggatgagga     11880
agtctatttg cccatcccat ccccaaacgt gatggtctga gatctcaggg acattaactc     11940 tccaacccctt ggagcttgcc ccacatatac aagtcaaaag aaatcctgca gaatgggagt    12000
cgcaggcact tgtcacagaa tcctgcctac aagtaacgga acaatgagag ctgtggccat     12060
gtaggtaaga cacttgtggc atctgctata gggtgagtta tggaaaactg acttttgaca    12120 taattttat tgtttttttgc ataggaatga catattttaa aatcaggaaa aaaaactgag     12180
ataaaaacac cataatatta ggttttctag agaaagaaa aagcttacaa ctaagccccc      12240
aaatgtgcgg ggaggccagg ggtctcttct caaaggggcc cttccaccta ggaaatgtct     12300
gccacagagc cagcagccct ggagatcagc tcacccgaca tgccggggga cagcaccatg     12360
aagaaagaga cagctaagac aaagcacagt tctgacattt ttattcactg atcataaata     12420
tagtctcatg agcattaagg tgatcatgaa tgatgtacta gcacctggaa catgaccatc     12480
atggagcact cactgattcc ccatcactgg ccaaagaagt cggggcatct tcctttcacc     12540
aagtgttcaa ctttggaggg accctccttc tggtgcagca attttattct tggcttgttc     12600
tcaacaatta aaaatcata aaagactgag tgtttgcaat aaaatatcaa agaggataag      12660
aagattttct gttcttctta aagtctaaag taaaaggggg aggtagggaa gaaggaaagg     12720
aaaggggaaa gatgtcaggg atctgccacg tttcttcctt cctccagagc attttacaaa    12780
aacaaaaccg gggaggtatt tattaatgct gtttggagat gggttgcgtc tctctgatga    12840
gccactcgag agcttcctgg cggccctgtt tctgcaattc cttcccaatc acatccctgc    12900
aggtcaggtg gtaattgttg agccagtcgc actgcaggga agagaaggac agacacggta    12960
ttcaccacca catctttaac aactggctac acaggtcaac agcaaaggcc ccatgtgct     13020 aagatcacaa gctgagagaa aaggtgtgca acacccttc tccttactca caggtaagta     13080
ttttccttgt gttctgtttc cccggaaata cataggacca gacttcatgg cttctggtga    13140
aaaggctccc agaacagttt actattatag acagcagtct ctaagccagt agctcctgct    13200
cccacctgtg tggcttcatt cccttaaacc tgagccatcc tgggaggtgg taagtggggg    13260
aatagccccg gactctgtga gaactcctgc tgagagagac actcgaagct gtcctgccaa    13320
cacactgggc tacatatcct atatccactg aaaaagctga ataaaaaact aggatcagcc    13380
aagcccatgg gtgtcttttg agtgtagctg cctagatgaa cccaaaacct gcggtggtta    13440
```

```
aagactgtgg tgcagcagaa tggcgctggg agtaaactta gttttcagac tctcaactca   13500
acatgccaca agagcaggag acaaaaaaga gagtgaaagg aaggacctgc tggcaggact   13560
tggtgcctgg gcaggggctg atccactaga catgatggca aaagctctga ggcaggaaaa   13620
agggtgaact ctcctccttg gttgtatacg ggaaaaggtg aagtctggag tgaagcaggt   13680
tttaccaaga ggacaacaag ccactctcat cactgtctat ggggtagct gtctggaagc   13740 tgatgagact gatagtgcca tggctgtgct tgtcataaat gagtcaaagg ccatttttgga   13800 gggcagcgat gttacagaag tactgctttc agggactaca atccagccag gtaccaaagc   13860
ccagctgggg tcaggatggg cacacaaacc cattaattac aagggactga gggcagacag   13920 ataggtggt gttaccaact ggctgtgacc cagccagggt tccaatccct actgagaaga   13980
gcctagtagc cccttctggg agtcaggaa gtgatggggg caggggagga tgtcaaaagc   14040
aggcaaactg ctatgtgtcc acagcaaggc cagcagggct acaaagcagc ctactgtcca   14100
aagcagctca acagtaaggc aacggcagca tcctggtgta agcctgggc cacagccaaa   14160 cgcccatggc ccttttggtt ggaagtaggg agggaaaagt gggagtgtgg acagcctcgg   14220
tggagcctga ggagcagcac aaggccctga cagtctgcag ctggccatat tcatatctga   14280
ccaaggtcct ttgctgccat ctggtgataa gtgatgacga tgcagaccca aaccaaaaac   14340
tccctaaagt gactccaaaa taaggctaa atagtaaagg gcaaatgacc agatatttta   14400
aaagccagat attttaagaa gacattatct gccctacaaa gagtaactgg ccgaaagaat   14460
agttcaatca tgtgggcatg caaggtcag caatgaaaca ctgggtaaca cagatccctg   14520
gtctatgtcc aatgtcacgg gagtagactg attctccttc gaggaaaaat ggcctggctt   14580
aaacttcctc atatactact tccctggata aaggggaatg tcatatggga gaaatgcctc   14640
ctgatgggta cactttatgt ggacaggaag gactgcatga cctagaatta cttggcagga   14700
atccatagcc ttggacttcc aagagtgcga aatgacttat tactggaaag ccccttgcta   14760
agtccctgga agctgtgccc aagggccatt acaagagaca ctggttccta tggggcagag   14820
ggattctaag cagggtgggt cccatgccca cctatgtgtt ttcattttcct ctcagctaag   14880 gcaacactta caggggctgg acaagagccc ctggacactg gaaggactct tcctgctgaa   14940
gagacacacc agacattgtg ctgataggct gagtttcctt ttccatatcc atctacaagc   15000
tgcataaccc acccggtatc agcaaggccc atgtgggtcc tgtgagtggg aatgtttagc   15060
tgaaccaagg gcacggatgg ttaagcagag gcgctcaagc acagaggaaa gctaagcagg   15120
aagtggatgg actttctcat cacccacctg tgaactggaa caggcagaag aggcttctag   15180 ctggagaat cccattccac agctcctgtg gaagggaagg tccttaaccc ccaaagaccc   15240 tttccttac agtgtcaaga acgaggccca agtgggcgcc agtgaggaaa tgttcctgcc   15300
ttgagaggca ctcaaaggcc attggctgcc tcagataaca aaatattctt attccgagag   15360
taacccaccg tgcttaccct gccttcggct cccaccagtc atttgctttt cattggaact   15420
tctgacccct gccttgctct ggaatttgtg tcctcctggc ttccagcttc ctggtttggg   15480
aactgttttg tctgtctagt gctaacagtt cctaccccat ttctgaccct tgtttctgct   15540
ctgaccttga acatctgtgt gattcttcag gcctttctca tgtccccagg actgccatct   15600
gacctggcct taccagtcca gggtctgaag gagttaagac ccataaccct ctgagctggg   15660
caagtaagca ctgttgtgcc ccaggctttg tgaagggttt cactgccccca gagtgaccac   15720 agtagtaacc gagaagggct ggtactatct ttcctccttgt ctgtgtgaaa acaggacata   15780
cgataataga ttttgctttc catttcctta atgtttcatg taacacaaga aaacaatctg   15840
```

```
gtatgtacag tggccaagag gccccaccat ccatctggct ttttgtaggg acacacatag   15900
gctcatattt gctaaacacg cctcactgca gctatggagg aatagtacag ccaaacaatg   15960
gcatacgagt tccacccaca aaccctacag ccccagaatg gctgcgggaa acaggactat   16020
ctccacctgg aggcccaaca aatacaggaa aagctcagga gtcctcagaa aacctagggc   16080
tttcagactc aactggccta gacctctaaa tttaaaaatt acaaagtgag actggattag   16140
agaatttagg atttagagga tggattagaa ctatttaagg tagtctccac ctcccctagt   16200
aacatgcctg cccaccaaga cttccccatt acctctttgt ctgtaagaga atccacatct   16260
atcattttgg tctgaattgg aaccaatgtt agaggttcaa aggtcaggct tccccggtta   16320
ttaaaattat actgcgggag aaagaagaaa acagatgctt ttactcctct ttactatgct   16380
gaagcaccat gaggtcattc caccagcatg ccatccctca gagccagggg taactgggag   16440
ccaagaagtg gtgagctggt caccacttTT cacagacaca caaggaacct gatgccattt   16500
tccaagagct cctccactgg gcaaacaatg gcctgtgcca tcaggaaagg ccaaacaaag   16560
ggtgctgagg ggctcccagc aacaggtccc aaggctaatg tctactgtga taggaaacag   16620
gggcaggata tggggtatc tgggcttagg ggcatctctg gttttggttc tccaggatgc   16680
agggtgtaa gtcctcaaaa tcattttat aacagtcaac tgtgtggtct gccttgaccc   16740
agccaggccc atcaggcgac aacacatcta tccactggag cacacaagaa catgtcgggt   16800
ttctgttcat ggcagctttt gggaataaga tgggaggtca cttccaagaa tagtgacttc   16860
catgccaaag cagagagcag atccccgcag ataacctcct tgtagacaca ggaagctact   16920
tccctccaat tgttcaattc caccaatgga ggaggcacaa acaggtcttt taggtaaagc   16980
ctagagccta aaaccctgca accttggtaa cactgatggg ggaagagggt gaaacacctg   17040
tcttgtattg cctttgaggc tgacccatgg ataactcagg gttcctcaac tttacctaat   17100
aaaagtcacc tggggagtgt gacaaaatta cagcttccag gcccccacc ctggaaattc   17160
tagggtctgg gaggggccct ggaaattagc gccttgaata ggcacccta gcagaagaga   17220
caacaggccg cctatagtaa actcagagcc ccaaatcatg tgaagcaagc atcagcctga   17280
gggtctgtga atcccagttc tagatcccag ttcattaagg attttctttc tggctttgca   17340
gggaaggagt gtggtttcca ggaaagtccc tgatatctgg agaagaaggc tccatgttgg   17400
ccccagaatg gcatactctt ggctccaaag acattaagtc ttcatcttcc cacactaaga   17460
aacaggaaaa ttttttaagct ttgcgcagtg gcagtattgt agccaatgag gtctatccga   17520
ggcgtgatta ttgctaatag aaacaggaaa attttttaa taaatcctca ccttggtctt   17580
cacaggaacc acaaggacaa cattctcaat gcgaattcca aaagcccat cttcatagta   17640
cccgggctct aaaacaaacc aaatcccaaa aatgagaagc agcccacgat gaagatgtct   17700
acagagagaa actttcactc cttggatgac tgccctactc caaggagaa gaaacgggtg   17760
aagagcccac tctatctggt gtaagagcct agagatgcca ccttctctca tatggccact   17820
tttttatagg cacttgaggt gcagaaagct agactctgaa gtccctgcac actggctaca   17880
gggtaaggag taaagtaaca gtggatccac taaataaatc atggttcaca tccgtaagac   17940
acaataatga aggcattaaa atatatttac aaagacttgg caatgacctg agaaaaggca   18000
atgtatcaag taagaaagca gaacataaga caagatgccc agtaagatct caatgattta   18060
aaaaaaaaat gctatctaca tacctgaaag accaaaagct aatacagtaa aacactaagt   18120
catgtttccc ctgagtggtt agattgcaaa tgattttcat ttttctttta cacagttccc   18180
```

-continued

```
atctcatttt ttctaaaatg aacatgtatc agttctataa tcagaaaagt ttgttggaag      18240
ggaaaagtat tgccaattta ctttaaacta attaaaaaat acaaacaac gaatagcttt       18300 caaaaaggct caaggatcca cgcatgccct ctatgtgagg gacacttacc atcagtgaca      18360
atcatgcctg cctccaaggg ctcatcagag aatgttttgt aactgatgcc gcaaggaccc     18420
tcatggacat tcaaaaaga cccaacacca tgtccagtcc cgtgcaagta atctaggcct      18480
gaatcccata aagctgaacg ggcaaaggag tcaagaaggt gacctgaaag acataaagag     18540
ccacttaatt gtatttgtac agcgctttag agattaaatt tattatgtgt gcctccagaa      18600
cgtgaaacag aaaccaatag gtaagttact ggagggttca gatttcagca cagcacaagg     18660
aagaactttc taacaatcag agctcctgag aaaccatcag agctcagtct gaagctaggc     18720
gatcatccat tcaggatgct ggttagcggg gatagacacc tacagcacac agaggccgta     18780
tcagacatgg acgttccctt gccagctctg cgaccctaag gtttcagaat tacaaagatg     18840
agactctaac cagactgcaa gcagacaggc aggcatgaca gatgaggaaa ctgaggccta     18900
gggagatgag tacatgtcta atctacccaa aagcaaggca gcccaggtct tgtcaatgcc    18960
cagtccaatg ctccacccac caggcctcaa gcaaagtagt acatagctga agtcagggtc     19020
ccagtaaaat aaatcctaag aatcccgaaa ggaagcactg gcccagtact aaagggcaga    19080
caggaggctg caccaacttc cactcaggcc ctgtgacctt catatctggt ttgtcctctc      19140
ctgggagcca tccacatgtg tcatccaata ccataagtgg tcaggagaat ggtgcacagg    19200
gggtactggg cccaatccta acccggctcc ctgaggcctc tgggctcagt cagtgggtta     19260
tggagactca ccccatgagc acctggctgg gcctgaagtg ggatggggac ctcacagtga    19320
aggaacgaca tgttctttca ctcaaacata gacatatttg attctcaaac aagaaaaaga    19380
gcctgccatg tgacagaatg caccacctac ctttggttcc agtcgggaaa acggctgcac    19440
tcacagctat gtggcccttg aggacatatg tgaagcattc ctgcaaagaa acccaggggg  19500
catgttgcag aatggggaca gatgtctaat cctgtagttt tctggtagtt cagaaaatcc    19560
tgcctgctaa agttttагc aatatcatag agaaaatgta agtaaaaaga aaaaaatctg    19620
gtggaaaaaa agcctggcca cgggaccaat ttcccagaaa atcttgaaat tcaatttagt     19680
agaagagcac tgtcagagag atgaccccac atgactttat aatgaacact ctgacatact    19740
ccatcatgtg agccttagaa agaatggaaa agtaataaaa agtactgatg accctagcta    19800
acattactga gctatcctct gtgccacgca ctattctaag cactgtatgt ttgatcccac     19860
acttcacgat ggaggcacta ctgttatcct cgcttcacag agagattcag tagcatgccc    19920
agatcacaca gtgcctaagt ggcagcatct ggccttggag ccaggcactc ttgcttcaac    19980
agctgtgctc cctaccacca tcctatcttc aggggttatc cccactgtcc ggacaagaga  20040
agtgctactc agaagtgtag cagcttgcca gtaaggtgca gagtcaggac taaaactcca    20100
tgctcctcag cctggttgag ctctttgaaa agcacaaaaa gagtcacacc aaaagaatcc    20160
tagacgcaag gtccaaattc ttctaaggca ctggtgaata caaatggaaa aggcaaggga     20220
ccaagacaat gaaacctgcc ccactacatt gcataaaacc cttttccttg gataatcttc    20280
ctgaaggagc tctcttggac aaacagattc acttaggtgc tcaatcagca tttgctgagc    20340
agtgactatg atccaggaac ttgctgggct catgggaatt cacagccacc cgggaaggtg    20400
ggtcctttta tcctcatttt tatggatggt gactgctttg ttcaacgtca cagagctagt    20460
aaatggcaca gaagctctga agccaggtct ccagacccct agtacacatc tctctgcctc      20520
acagctctct ttccccttc catgccaatc ataccagaaa cttaatagag tctgtcattt        20580
```

```
cagaaagttt ccagagagtt aagcctgtaa ataagaatct caaaaaaaga aggggtggc    20640
cttcaaaatc aaatctaggc actgcttata aagcatgtat ttcactatct catccccagc    20700
ctcaaaggca tttcctgact caagagaagg ccaaagctac tatatttaaa cttacacctg    20760
agctgcccta accttagcag aatgctttaa aaatttctcc aaatgtctta ttccaataat    20820
tagttaaatg aacctcgtaa agcagataag cctgactcca cagcaaggag caattttact    20880
accccccatg taatttttac ttctttatac aatcccttt cataaaagca atgctcttct     20940
taagaaagca gagaggacct cttgagtttt ttacctccac cttaccttct cgtaggctgt    21000
aggggtccca aaatgcattg tccgcgtcac atctgtggtg ccatcccttt ccaaaaaaag    21060
gacaaattgg tttcccgtca aaataagctt taagtcaaat atgacacagg caagcatgtg    21120
gacaagtgag aagccccata caatgctggt gggcatgtaa aatagcacag ccatctttgc    21180
aaatagttcg cagttcctta aaaggttaaa tatagtcacc atatgaccca gtaattccac    21240
tcctagttat atatccaaga gaactgaaaa catacatcca cacaaaaact tgtacatgaa    21300
ggttcacagc cacattattc ataatagcca gaagatggaa acagctgaaa tgtccatcaa    21360
ctgatgaatg gataaacaaa atgggggatt atccacacag tgcaatacca ttcagtaatt    21420
aaaaagaaat ggaatactga tacatgctgc aacatggatg aacctggaag acattgtgct    21480
aaatgacaga agccagacac agaaagccat acataataca attctatttc tatgaagggt    21540
ccaaaatagg caaatccata gatacagaaa ggagagtagt ggttctccag ggtagtggaa    21600
aagggggtag tgaccgctat tgggtatgag gtttcttttt ggggtaatga aaatgttcta    21660
aaattgattg tgctgatggc tgcaaaactc tgtgaatata taaaaaaaaa taattgtata    21720
tttttaagtg ggtgaattac atggtacata aatttaccc caatgaagtt atttttaaaa     21780
atgaaacaaa gtgtgaatgc agggatggct aaataaactg ggagtgacgt cagcccctga    21840
cacacgcatt cttggtctac agcataaggg ctgtttcacg agagacacta tcactggggt    21900
tatgaacaag acagaagaag gcaaagaaaa caggagccca tctctagcaa aagagggcca    21960
aaacccaact tctcctgtta gaacagcagg gggtttcctg gacagagacc ctaaaaatat    22020
ccaagtacat atcttaacac acactagact atatccctga catagaaagg ataacttcta    22080
gaatcctgct aaaaatttag aagtgaagaa aagtttacac cattatcaag caatccttag    22140
ctctaggctg atattattaa caccctgtg tcccaaggcc aggcatggtt gccacgtaat     22200
tggctgagct cattcaataa ttaggtcctc ccttagccat agtcccaact tcagtgggga    22260
atggagcagc actaaaaggt cttgctcggc tgggcacagt ggctcacgcc tgtaatccca    22320
gcactttggg aggccgagac cggcggatca cgaggtcagg agatcgagac catcctggct    22380
aacatggtga accccgtctc cactaaaaa tacaaaaaat tagccgggcg tggtggcggg     22440
cacctgtagt cccagctact tgggaggctg aggcaggaga atggctgcaa cccaggaggc    22500
agagcttgca gtgagccgag atcacgccac tgcactcctg cctgggctac agagtgagac    22560
tctgtctcaa aaaaaggcc ttgctcgtgc cctcttaatg cagacagggt ctattcttac     22620
tccttctttt gggttccgta tcaagaccca accaaatctt gggttcttct ctgagaaact    22680
ttgttccaga gatgatagcc gtgaaagcag caaaacatgg agaaagaaat tcagaaatgt    22740
ggggcagcc tcatttctc atttattcat tcaaaattaa tcccttactt cataaggccc       22800
tggggcagct gagagtacag ggaaccggca ggcggttcat gggctggggt ggaaaacttt    22860
caacggttcc aaaagcttgc tttacttcac agttgtttac ttatattttt aaaacttcca    22920
```

-continued

```
gccaaggact gtaacatttc tatcaaacag tcttttgtga gaacagagtc acaactgggc    22980
tatttcaaat aggggtgaaa aaaatgacaa gacacaggaa cgattccatt agtggccagc    23040
acagagggcg atgaccagct gagtgctctc agctggagct cagctgtcca ccttctccac    23100
tgcctcgaat ccatagtcaa gttccacagc agtcctggtt tacttacttg tattgagcac    23160
ccgagtcaat aaggtacacc tcatccaggg acaaggtcct attcgtctca gggactggcc    23220
taacaaagtt aattaaaaat taattattcc acaaatgtaa acacttagtg aatctgggag    23280
gaggacacac aagagctctt tgtactattc ttgcaactta cataagcctg aaattatatc    23340
aaaatagaaa gttatgcaat aatgaattat ttcaactaat attaaacttc tacttttcaa    23400
agatccaatc aacctatctc cccagctgag ataaagagct caacaaagga aaagtaacac    23460
atttctttat gtctacctct gtttgtgtct gaaacaaaat aggtgttcaa gagataattc    23520
taaaagctaa aaaatgaga acgattagat gcaacaggac ctagctagag tcctgggaac    23580
tgggacagga gcagcctgga gtcactgcag ccttgcttgt ctctgggagc cccaggcccc    23640
tgcctcagcc tccaggcccc tccttcagcc ctgaccccag caggtacctc cccactcgct    23700
ccccagactg ctagacaggc aggagtggat gtctcaactt gggagaaaaa ctaaaggaat    23760
tttgctggga aaaggaatgg atcacgatat tcttctgctt caaacaaaca tgaggtattt    23820
tcaaaaagtg atctctttcc ccacaccgtt ttcaaaacaa tatcactgca ctgggaaaca    23880
cccaaaggga tgagagcact ccaagtctct gccctgcagc tgaagtgagg ttgtcctcca    23940
tttccaggta ccaccccctc ttcagcaata agggcaccag tccacacaca agctgaacaa    24000
ctaaaaaaga caaccagtac ctccagaacc ccgcctctaa acaggcttcc aaccacccac    24060
aatgaagaaa tgccaacgca gaggcaaatt tcttccactg gcatgaaact gtttaatgtt    24120
ttaattatac ggaaaattct aggatagtat ccagccagga aattcatcct gagttaaaca    24180
aaaactgaag tccctctgat attttttatgc tggaacagaa gcattaagtg aggaaactgt    24240
actgtcccat ctgtgactgt ctcccacaca cagcttcaaa atctgcccca agactaaaag    24300
ctctaaaaac aattattaaa aggggggaaaa aagtgtgtgc ccaagcacag tgttcttttg    24360
ttggctgtgc atgtaacaga tggggatgca cagaactcaa aatacccagt gcaaagcaaa    24420
gcggtttgaa ccaggcagag ctgaggctga agcccaatgg ccacacctaa tgacatttcc    24480
ccccatctcc acaggaagat ctgtcagtcc tagacatatc agtgcccctc tgtctcacaa    24540
ggaagggagg ctcggccctg tgggtccatg ggttcttgta gaccacgtgg taaaaaaacc    24600
acatactggg atgccaggct tcaggctcag ggggacagga agagagggta ctgattatct    24660
ctccacccaa aacaggttgc ctcacaacct actactaagt tttttttttgg tatggaactg    24720
atggagctca caagatgtat ggactagtac aaaacagctg ctgttaccaa gaaagaaaac    24780
tactcaaaaa ttccagtcat gggccaagca cagtggctca cacctgtaat tccagcactt    24840
taggaggctg aggcaggagg attgcttgag tccagaaatt cgagacaagc ctgggcaaca    24900
catcaagatc ctcatctcta caaaaaaatc taaaaattag ccaggagtgg tagcacatgc    24960
ctatagtccc agctactcag gaggctgagg caggaggatt gcttgagtct aggagttcaa    25020
agttgcagtg agttgtgatg gcaccactgc gctccagcct gggcagcaga gcaagacctt    25080
gtctccaaaa aaaaaaaaac ttagtcatca agatgcaagg gctatgcata cagttcctgc    25140
agcttcaaaa aggaaagagg gacacccatc tgactaccct gcagagaatg ccagtgccat    25200
actgagccta agaagaggct cccaaaaggc agaggcttgg ggattgggag aaaataaaat    25260
cttagaagtc ttatttccct tcattttaca gtctcaacag acagatgaag gtgggcacag    25320
```

```
aggcctctgg taaataatg tctctcccct gctcaggctc ctgtgcagaa gcagcaaggc   25380
caggcagcat gctcctccgc atgccttacg cgtagtgaat gatggcgccg ttgggtcccg   25440
tactggaaat tgttgggaag ctcaggtcca caaagtctgc ctgttgcctg taacagaaag   25500
acagaaagca gagtggctta aaggttttta ctgtgctaag attcagggcc cttccagcct   25560
cattcaacta gcaagaaaat cagcacgagg ctcctgggtc cccccaaatg gatccttacc   25620
tgcgaaactc ctcagctttg tcagcagctg agatctctgt cacaccacct ttgggaacct   25680
atgagaaaat tgcttataaa tcatctggtg agataaattc atgtgtgcct cttacaaatt   25740
agaggaggta cattaaaagc tcactttttc ctcaattgct tcatcccaac tgaccaatct   25800
acaggacaca tctttagcaa gggagaactc ccaaaggctc tcaccaaagc tatctaaaat   25860
ccaatagttt ctattcattt aattttcac tcaactattg tgcttcagta ttttatccta   25920
aaacctccca aaacaacata tctaagttta aaaattcaaa agcatcccct cctaagaaat   25980
catcgtaaga aaatcattct agagaaataa aaagataaa tgcggagaga ttattgcagg   26040
attactgata acagcaaaaa attaaaaaca acccaaacat ttaaaaatag gaggactggg   26100
ttagtaaatc agaagagcca ctagatgcag ttttcatttg gatcctttt taaggcctca   26160 atgtacatgg aaaatgttca cactatgatt ctaagagaat aaaataaaac acaaaatcat   26220
atctaagcca ggtgtgatgg ctcacaccta taatcctagc actttgggag gccaagatag   26280
gtggatcgct tgagcccagg agtttcagat cagcctgggc aacatggcaa aaccttatct   26340
ctacaaaaaa atcagaaaaa atcaggtggg ctgtagtccc aactaatcgg gaggctgagg   26400
tgggaggatc acctgagctt ggggaggctg aggctgcagt gagctgtgat cacaccacta   26460
ctctccagcc tgtgcaacag atgagacccc atctcaaaat aagaaaaaaa aaagaaaaa   26520 aaatttatct gcacactaag agacatgtaa aaataattta tatttttaaa aataatttac   26580
ggccaggcac ggtggctcac gcctgtaatc ccagcacttt gggaggccga ggcgggcgga   26640
tcacaaggtc aggagatcga gaccatcctg gctaacacag tgaaacccg tctctactaa   26700 aaatacaaaa aattagccaa gcatggtggc gggcgcctgt agtcccagct agtcgggagg   26760
ctgaggcagg agaatggcgt gaacccagga gacggagctt gcagtgagcc gagatcgctc   26820
cactgcactc cagcctgggc gatggagcaa ggctctgtct caaaaataaa aaaaataat   26880 aaaaatgtaa taataataat ttacataaag tccaggcatg gtggctcatg cctgtaatcc   26940
cagcactttg ggaggccgag gtgggtggat cacaaggtca ggagttcaag accagcctgg   27000
ccaagatggt gaaacccat ctctactaca actacgaaaa ttagccaggc gcagtggcag   27060
gcgcctataa tcccagctac ttgggaggct aaggcaggag aatctcttga acctgggcag   27120
cagaggttgc agtgagccga tcacacacca ctgcactcca gcctgggtga cagagtgaga   27180
ctccgtctca aaaataaaa taaaataaaa taataataat aatttacata gatgaacaat   27240
caccagaagg aaacatgagg gaaaagtta cactagtggg aataaagaca atattttctt   27300
ttcccaatta aagagttgtt tatacaatac ttaaagggaa catgatattg tttaataaca   27360
ccacagagaa accaccctct tgtcaactag agcaagaaat taatggccaa gagtcaattt   27420
aatataaaaa ggctcaaggc ttaaactgaa gttcaaaatg tacacaaaga tcttttttctc   27480 ctaatacaat cagcttgcct ataataatat tataagactc attttttcctt ataatgaaat   27540 tccacttagt tatgattccc taacccaaaa agcatccact ctattatgga acttttcttc   27600
attcttggga ctattttcat aattaaagga attttgaatc tacacccacc aaatttccat   27660
```

-continued

```
agggaattat taaaatagac cccaaaattt gatgaagatc tcacatctta gagcaagaaa    27720
ttaatggcca agagtcaatt taatataaaa aggctcaagg cttaaactga agttcaaaat    27780
gtacacaaag atcttttct cctaatacaa tcagcttgcc tataataata ttataagact    27840 cattttccg tataatgaaa ttccgcttag ttatgattcc ctaacccaaa aagcatccac     27900
tctactatgg aatttttttc attcttgtta ctattttcat aattaaggaa ttttgaaatc    27960
tacacacacc aaatttccag agagaattat taaaatagac cccaaaaatt tgatgaagat   28020
ctcagatctc atggtcagca gagcatggga gatgcttaga gttagaatca catataggta   28080
ggtctgaata atgtatatcc acatattaaa caaagactaa gaaccaacct ctttctccag   28140
ccagttaaag agttcacaga gagcaacagc atctttaatc tgtgcaaaca atggagacat   28200
tttttaagtt atcactgaaa atcacgtgac cagattcaga gcctagccct aatgcaatac   28260
tgagaaggct gtacctgcag ggccacacat catcagcaac cagagctttta catgtggaca   28320 tttctgggaa gctggtgtgt gcagcaactc ccattatcag ggaaaggctc ctctgctatt   28380
cagtagttca ggtacaatca ggaagggccc cacctcagag cacaggagc tcctccaaaa    28440 ggttaactta aaggttaaga accctacagg ggccaggaaa aaacaggcca ctatcaaaag   28500
ccacctctgg gcccaaaatc tttcttcatc agcatcacgt catcaccatc atctacactg   28560
tgaacatcaa tatctccttt tgtattgtgt attatacttt gtaaagatct aatccatcaa    28620 gtatttatt tcattccctc aataactcct cctggaaggc caggaggctg aggctcagag    28680
agattctaac cttgtgccag gctcaatgcc acagaggagg tgaaggagcc gggccttctg    28740
accacctcac atcccatctt ctgcaccagc tcctctactc acgtgagccc gcctcatgcc   28800
ttctgactca gctgaattct tcacagcttt ggcgatgcag atgggggtgt aaggcataca   28860
gcagcggtgg tcctagaggc aaagggcagt agggtgggaa atcaaaccgg ctccacccac   28920
ccaagaccaa ggcaacaacc tttttgctca gcaaaactta cttagacaa atcatttgaa    28980 gagctcccac tggcgaccca tatagctatc ccctgggcc caacgacct gtccttttg      29040 attgatgacc ctgagcttaa gctcaaccaa aaagagtaag tacatcaaac aaggtgtctc   29100
tcttccatcc ctcactccct tagctctttg agactgctgg ctgcctgccg tcagcaagac   29160 attgcttttcc aagccactgt ggttgtggtt agagttcact aacactgaaa gcttgaccga   29220 aatcacccctt ctcttgctgt acaaaggggg ctttttctcc ctgtctagcc atgcacatga   29280
cctgatgagt gaggtctcct gctccctccc ttcccgccca gtggtcctat ctcagctact   29340
gataataatc tgatcttgaa gggctggaga agaccctttc caatttgaga acaagttaga    29400
atccagcaga ggggcctcag cacacctggc acttgcacaa agcttctaaa attgcttttg   29460
tgatcttatc tcctttttctc tttctctcca gagagagagg agagagagag aggaggagtc   29520
acactgtgtg tgatgatggc aggggtacaa tggcaagcca gatctagaga gccaggcctg    29580
gattcttccc aggatgcccc actgctcagt ggagaagaaa ggcatcact gggcttgcca    29640 aaggccactt ggcagccaga ggcccagggg aggacagtag aaaagcctac ctttaaagag   29700
gcctggattc cagtcccatc tcagacccta atgaaaatga ggcaacaagt gtcagctgct   29760
tagcactgcc cagcaagggc tcagtaaagg gcaaggctat cactatcact tgaatttgac   29820
aaatccccaa atccccaact ccccaatcct ctctgagcct caagtgtcct tagctataaa   29880
atgtggtgcg gcagaaggag ggggtagaga agcatttccc aagcttcaag cattcttata   29940
ccacctgcac agctttttacc ctagcttctt aactgctgta cccttattca cttagtactt   30000
tactttagac catctttaaa tcagctttat taaattcaac tttattttaa ataattatat   30060
```

```
catgaactca tgctagttat gtttttcta ttatatgcta aatgctgtta aaacagatat    30120
atttaagtaa acctaaataa taatgtgtac cacctaaaat aatctctcat gccacactct    30180
ggaaaacaca agactcaaca agcaataagg gccctcaggc tcttgctatg gctccagctt    30240
taaggcctca tccatggaga ccacagttct gatccaacag gcagcctcag aaatctgcct    30300
gtgctccaaa gacaatacca gaactgggaa gggggtggca gagtttagat gggccaaagt    30360
ggggtcacca accttgggga tggtctcgct cacagcatag ctggccttgt cactgaccca    30420
caccttctcc cttggggaga ggtcagcaca cagggccttg agctcgctca ggatggactt    30480
gtagggatgc acctggatcc tgtattcggc ttccagaccc aagtcaagaa gcaggtgctc    30540
cttcacactg ggggcgtcta tgcggtcacc atcaatgaag agcctgcaga tggaggagag    30600
gtgggtggca gaaaaaggag ggaacatgag tgagaggtgg caacacagac acacatacac    30660
atcaggctct gtttcctggc aaccaaaacc aagccccttt tctctcctcc ccactccttt    30720
cccaaatcct gccctccaag gtgcattccc tgccccatc cacccaatct gccaagccag    30780
aaatctgggc agtgtcctcc ttcactgatg accctcttcc cgtccttcat taagaccttg    30840
ggacccacag cctaaatctc catctaatct gtccagctca tctacagcct cgcccagtca    30900
ccactcaggt tcaggtccca ccatctctca cttgggttag tgccacagcc tctaagtctt    30960
tccccatcta ccgatgtttc agtcataata ttctttacaa cttgtacatc taacatgtgg    31020
ttccctctga aaaattcgtt caatagcttc ccactattct tgttcagaaa aagaacccaa    31080
gctcctgaat gtgcccaca aggcctctct tttctgtggc ccctgctcac attctggcct    31140
cactatgttc tgacctcact gaaccacttc aggtcctcca catgcactgt gctctctact    31200
gtccagagtc tctgaaaatg ctgttccctc tgcttggatc atggttcccc gccctcctc    31260 accctgccat tcacctaact cacccacatt tatccttact ctctgcttca aaatattact    31320
ttccccaaga gtctgctctg atctccaagt ctaggtcagg cccctctcgt aacacctgta    31380
tctgtcccac aagcagactg gtgcccactt atgtgcccaa atactttaga agaggacat    31440 gctcatctcc ccaactccag ccaaggaccc cgtcctgttt cagtcaccct agcacctaac    31500
agagaccctt agcacatcac cagcacttaa taaatgtgtt gtcttaatgc aaaaagctat    31560
tgaaatagaa cagtaatgaa aagaaggcca cacgaaatgc tttgaaaaaa taactgaca    31620 attcaacaaa gcgtagttgg agggttttc ccatattatt tttgaccttc aaaatgactg    31680
ggtttatttg cattgtggac ccagaattgt ataattgagc atatataccc cttaacactg    31740
gctgctagaa aacttgacat caaatgggtg gcccgaacta tagacacttt catgcgtttc    31800
aaaccatttt gggggctcaa agagaggcag gatataaata aacacctact gctaaggaaa    31860
acaagaaggg aaaatgttaa aagggcaaga aaaagaagc acatcagtga aatatcaggc    31920
agtgatgggt gggccaggac cagaaagggc acactagggc tctgaggagc tctggaaggg    31980
agttccagat gcagggcaaa cactcacatg atcgtctcta gtcctatgat tgcgtaggag    32040
aaaaatactg gattgtgctc cacatctgat cctcggagat taaatagccc tagaaaagaa    32100
atcaaaatcc ctgtcacctg tctgacttaa gatgttaagg ggtcgcttgt agcgggaggg    32160
aagagcttca gcttggagtc cagctgctgc gcaaggattc agtggaatcg cacagaaagg    32220
ctggaagcct gactcccgtc tggttccacc tctgagctgc aattgctcat gtccaccacg    32280
tgatggcacc agagctgttt ctcaggcttc cacatcactg cccggagaag ggaataaaag    32340
ctattagttg aaatcctgag aactgccccc acaaggagtt gaaatgatcc acctagtggt    32400
```

-continued

```
gacctgccag gcctggcctt gaagccgaca aacctctggc gctcccaaat aaaaaggaag   32460
gagacgagca ctctctccct tctgaggcag atgacctagg gtagaaaaac tgagaccctc   32520
ccacaaggga agccaggcaa gcctcctctg taagggtcag tgagccccat ggagacggag   32580
cttcctgtca gaggtggaaa gaaaagcagt gagtcagcaa ggctgcagct caccaatgaa   32640
atcagagcct gcagcccacc catgggtctg ctctggcacc acgactgggt gggggacctg   32700
cggacagcca gtaacagtga tgttgctgaa cgtctgagaa ctagacagac caggagagag   32760
cacagttctg gtcccaggac ttccagcttc cgtcacttgt tctcatgagg atcagagcaa   32820
aaaaacgcct gggcattaaa agtataacct ctattttaaa ataatggctt cttaaagtga   32880
tgaggcacca ttttttacct atcatactag cacttcttta aaaatgacag tacctggtgt   32940
tcaggtgtgg caagacagac aaattcaaat acaaaggtgc aaactttctg gcagacaaag   33000
ggcaagatga gtcaaaagcc ctaaaagcca accagaaata ggaagaaaat tatcaaacac   33060
taagacatgg attcatgaac caagattttg atggtagcat cataataaat tacaggatta   33120
ctgcaaataa cccaaaggtc atccttaggg aaacagttaa ataaattatg gtataaccac   33180
atgatggagt atttaatact cacttaaaat tatgcttgta tatgcttata gtgtactgat   33240
acagtgaaaa aatcaggcta taaatgata tatgcataga atattgacac tgattatctc   33300
taagtaacag aatttatacg tgattttttt tttcttcttt ttacttcctc tgcatttttcc   33360 aagtttctta tcatgggatt gtgtttttgt tacaatcagg gagagagaaa agttttacag   33420 gtgttttttct ctgacgttga gatcattaag ttaattaggg atgtaagtca ctgacacact   33480
tgacaatgtt ttgtggatgg aagatgcagg gactgaagag agaggacact gcagtagggt   33540
ctcattctct agtgagaagg caaaaagata agcagtgcc tcttctcagt tgccctgggt   33600
caaatccact cagaaaccag aagacaggac aggaaggttc aaccagattc cgtcaggttt   33660
tagatgaaag aaggtgctga acaactgcat gaaggtgggt taaggtccaa agactgagaa   33720
actactatta catcaaaggg cttggggagg aacttttagt tcctagtttt ctgaggtaga   33780
aatgctccca gaacattctc actataaaga ccttaggaaa ccacaggaca agtgtaaaga   33840
aagaaggcct ctcctatgag cccacttcta cacctacaga ggctgacaga cataaaatat   33900
ttgtaggaaa tgcccttcct cagaggtgcc atggtcctga gggactggcc agaggtgggc   33960
atcacccagc tgtaatactg ctctggacaa gcctcactcc cctccccagc tccctgtaat   34020
tctttctcct tcatcctagt tggcatctcc tatacccatt tggtgacgta gtcttcttct   34080
tattccctgg ccactcagaa agttgaatgg catgaacaca cagatacccca gagacccaaa   34140 ggagagatcg ggtaacatgc ccaaacagcg aaaccagagc actcacacgc aatctcatcc   34200
aaggcagtga ccacaaacca catgacgttc ctctcagcca ttttcaaccg aaggtctgca   34260
accttgtcct tccaggagat gcctgcaaga aacaaatgtg ctttaactcc agccctggtc   34320
ccagaaagcg gtaggaaccc agtgaaagaa cctaccctaa acatctttaa tcagcaccat   34380
ttcttacagg agcacgctac ttaaacaggc aggaggcctg gattcaagcc ctatacaaga   34440
agtgtccaag ccacttgact gtcgtgagcc ttgattgcct caccagtaaa attcattcat   34500
ttacgcatcc cacaaatgcc tgtgtaacat ctagatctgc caggcataga tacgtgccag   34560
gcactctgct ggtcactgtg gttacagatc tgagccagac ccagtccctg tcttcatggg   34620
gcttacaata tagaagggaa gacagataat taaaccagca attaacacac tactgtaaat   34680
actgatgcaa caggggacac acagggacct atatcaacac actacccagc aaagggaact   34740
cacccagtct cagggggtcag gggaacagca cccaccactt gatgttcctg ggggctgcaa   34800
```

```
gacttgcctt tcagtgctaa gacctaggaa ttccctgtag tctgactcac tgtgattacc    34860
acttccaaat cacacttgcc cttttcagaca ctgccaaggc ctctctgttg ctctgcaaga   34920
tgaaatcgtg gtgctagagg agctcacccc attgccacca caaccaccct accagggcag    34980
cattcataac tcagggaaca gccacctgtg agcagggtgg gcatctgtct tattcactca    35040
gcacctcgca cagcatcctg cagatagtag gcacccaaat gtgtactgaa caaaagcttt    35100
atcagcaaca tttgctctcc cctctcctat aagcaacaag tcagagcttc tgctctagtg    35160
aaaaaaactt caaaccacgc tgatggaaaa tatttagctg accctgggcc actcactgga    35220
cccatcctcc ccattccgca ataccctct ggtgaggatg tcacacaaga aagcaggctg     35280
gggctgcccc cacacccagg gctgcactga agatcagttc gggaatgctg tttaaaactt    35340
ggcccagaat ctaggctgtc acgctttctt cccaggaccc ctctgggcaa tctgcctaca    35400
ttccacagcc atccccatc tacctctgtt tctacagcaa gacgccctcc cctgcagccc     35460
cacctccagg cctctctctc tgcccctca ctgcttcata aatccacaca atggttcaga     35520
gaacatgctg cttacccatc actatcgcac aggccaagga acacaccca caccccaaag    35580 cctctaaagc agaaggtaca agatggagga caaaggccta ggaaggtaaa tctacaaatg    35640
ctgacataag aagggaaatg gaacctagaa acctctatgc tctatttcca atatcaaata    35700
cgttcgagtg gcagttagca gctgagtgga taaaaaaac tcagtctttt cagcagcacc     35760
caaaagccca cccaaacgag ctttgcgaaa ataaccaaag ccaaactaag tggcaagtag    35820
gtggcaacag tggaaacaaa caaagctcct gcttcttcaa atatcccact ggggcagagt    35880
agggcaaaat cctcctgtca gctccaactc gacttggatt cggaggacga ggttggagac    35940
aatagcaaga ggtgggggga caatggcagg ggccctgctg ggcagaacca ttgattctga    36000
cctgtgtaat ccaggcccag tgtgaggaga ggcttgcaag ggcgctcagg acggtctgtc    36060
cagattttgt caacgaggtt ctccttgaca ggaatgaggt gatggccggc acttctcaga    36120
actttggcca ttttcttcca ataatctgag gagacacatt gtggcccagc catgagccga    36180
acgcccattg cagcagggca gggagcaggg ccttgaaagt ccagaacctt cagaaaggtg    36240
gtcctgccat ggcccagagc tgggtgtgca ggatgaggaa ctgtaaaagc acatcttcac    36300
caccagtgga actcttctct tcaccctgac ctctactata aaatcagtca tgctgagccc    36360
cccagtgctc cacaccccac aagcaaatga ggagaatgga ggggaatcta gaagccactt    36420
ccttacccaa gcagaaaggg accaagctca cttacctgta ggaatgatca aggggtccac    36480
accaaccctg gatccttcag gaagcacact caccagccag tcttcctgag ttggtgtgtc    36540
cttcagacct acaggggaa gaaatgataa gaaacaattc ccagtgggcc cacgctcatt    36600
atcccaccag aaagatacaa ttctctaaca tcatgatagc agggtcttta ttaagcagct    36660
tctttaaagt ggattgacag gacttagaaa atctgaacct cccttaatcc tggaaggcta    36720
cagagaggga gaagtgtaag tttttgtgta tgaaaacat aagacaaggg tgagacagaa     36780
gggaaaaaag tatgattttt cacttgaccc cttgtaaaaa tatcttgggg atcactgcca    36840
cgtacacaca tggcgtcacc acaaagattg tctcctcagc gttcagtcac ttccccacta    36900
ctggtcactt gatgagaatt tgggcagtga tttggtgaag tctgggaact gggagactcc    36960
cacatatcac ataccaggta aggtgataac atgctcccag tgcccgcccc tcatctgcaa    37020
gggcagggtg gccaagagaa ggccgctgcc ccataaccag cctctgaata gagggctaag    37080
cacaagtctt ggcagcaaag agatctttcc gaagatttta agagaggcac acaggcacct    37140
```

-continued

```
gtccggttgt ctttatttat ttatttactt ctgaagacag agtctcactc tgttatgcag    37200
gctagagtgt ggtggcacca tctcagctca ctgcaacctc caccacctgg attcaagcaa    37260
ttctcctgcc tcagcctccc aagtagctgg gattacaggc tcaaaattac catgcccagt    37320
taattctgta ttttttagtaa agacggggtt tcaccatgtt agccaggttg gtcttgaact    37380
cctggcctca agtgatcctc ccacctcagc ctcccaaagt gctggccatc ctgttgcctt    37440
taacatgagc ctctgggttc cccaactccc aggatgagag agccctttct gtttctaaga    37500
cgctagtcat aggacactat atcagcctcc agaatagaac taaaattact tctatagtcc    37560
agttttcctt taatctaagc caacaccttc catatctagc cagttatctt tgaaatgtat    37620 actttttta accaatgagg ttttggccaa acaattaaca tcttgataaa atatacatat    37680
atttagagta aaagttcaca tattctaaaa cagtagaaac ttatctttac tattttctct    37740
actgactact gatacaacca cataaccata aagggaagt gcaaaggttt ataaagaaag    37800
aagctcatga attccaattc taaaaaactg cctagaagct gacattgagt ttcattctgc    37860
tatttgattc tttcctattt tttttcaaac cactaaacaa gccacttatt aatacagttt    37920
ctcctaatgc cctagtacac tacataatat aactttcaca ggatgaagtc atgtcatttc    37980
ctagcagaca gatcttcggc aaaaccccag ggatgaatca ctcactggcc aaccaaaccc    38040
accagaatct ccctacacag aagactcgac tgaggaaact aggaaggagc ctggaggaga    38100
ggaggactca ctccctctgc cacccccttg ctgccacata cctacattaa ggaacaggca    38160
ggcagtgttt gcgcctctga cccccaaaat gctaacagac ttaagagctg gaatccgtgg    38220
gccccaaaga gagatgcctg ctccccaggg ggacacaatg atctactggg tgcaagaaga    38280
aagtaacaga gcttctattt gtatttattt tttataaaga aattacaaag ttagtttttg    38340
atatttggaa tatagaggaa cactagcaca tataaataac aaataaacaa acatacatac    38400
atgttgcggg tgcttgactc ccattaacag aagcacacaa acaaaaaaat ttaaaggcca    38460
ctagcttgtc catttataac agccagcttc aaatgcctgc ctttgtgtgt gtgtgtgtgt    38520
gtgtgtgtgt gtgtgtgtgt gtgtgtgtga gagagagaga gagagagaga gagagagaaa    38580
gggaaagaga aatcaactgc agcaacaggc aacaatctgt agctttggtg tttttatatt    38640
tatgaaatga ttttttgagaa atagaaactt aatccaatgc caagacaaaa atgttccttg    38700
ttcctcccta agacaaagaa cacatgtgtg tgtatgtgga gggtgtgtgg catacacctg    38760
agtgcacaca cccctcagtc agctggctgc ctggatctca aggtcatggt ctagtcctct    38820
gtttcctgct gtgagtctga ggactatttt cttttcctcat tatttcctac aacaaacaag    38880
aagcatcagg tattttgttt catcttctct ttctcacttg gcccttcctt atcttctgtt    38940
ctccaagttc aaaattcagg aagcaaagac tttgtacagt ccctaaaacc gtgtttctaa    39000
agactatttt aatgacagga aagtacacac ggcagaaaat taaatgaaaa cacagagtat    39060
atacacacat tattcaataa acattgatct atatgctttc cacatagtaa tgctttaatt    39120
ctcaccactt tatatgttac ttactgtgat taacccattt tacagatgag gaaactaaag    39180
cactcaagtg aagcgactag cccaagcaag ttccagacct gttcgcttgt cctgaatgct    39240
gctcttctcc agagctaagc ttccagaagc aaatccaaga tcctcagaga gagcctcagg    39300
ggaaagcttt ctggcttctg ttgccaatga ctccttgcct ttatctcact ctgaatcatg    39360
aggcagcaaa tagtagaagg cccccagtac aggagtgaaa tgcacagcaa tgtgatctgc    39420
agcaaatcaa ctgtcctctc tagccctcag tttcccctca gtaaaataag tatcctgaac    39480
cagcgtctcc aaaattgaat gcacattggt acgtatgtat aggcatgcca tttttttttt    39540
```

-continued

```
tctcagtttt ccttggattc tcaaaagggt ccatgactgc ataaaaggat taagatccag   39600
gagtcctgag gacctctagg atccctgccc agatcaggcc aactaagttt gggctagcca   39660
tgcctgtacc cacccatctt cataagtgtc cagttgctgt ccatttgctt ggcagcctgg   39720
agaaagtagc gcccgtcagt ccacatggct gcatgctctt ctgtgatgat ggctgtgcct   39780
gaagcagggg agaaaaaaaa aagaagaaga aaggtttcta acaactgctc aaaagctgca   39840
caaaatgaca gtagacaggc aagagcagta agaggcatca gctcctagtg gggcagatgg   39900
gtccttgact ccaaagaaac ctctgggcaa gagaagacca cactactgaa aacaagctgt   39960
gtgtcaagct ctgaaagaac agtcctgaga cccaagctac ctggcactgg tccctgcaca   40020
aaaaggactc cacttgcaca gtatgagtca agaacagaga atggagaact gtagacctat   40080
ggccaaagtg gtctcgtata atcaacaaga cacagggagg gatggttcct gctcagcaat   40140
tacagccact cctctgctcc accagacacc ccagggagc tgtttcacct ttcctggaga   40200
aagaccaagt gggccctatg agtgttcctg ctgtggtcac tagcaggaag cttatgcctc   40260
ctacctttat ctgccctccg ttcccacagg cctggcagaa cttggggttt tggcagaggt   40320
gtcagccaaa gccaatccta atgcgccaac caacacaagc acttacgcca aggaagcag   40380 catgctaacc atgaggggag gggagctccc accttgtcca gcttgcttta gagaacaaac   40440
ctgaagtggg gagtccaccc taaaactcaa aggcataatg gttttgagga acaccaatgc   40500
agcttagagt taacctttgt tatttaagcc aagagtgaaa acagaaacca aaagccaagc   40560
acttgggaga attatctggg accaataagc taagagagga ggttctgaaa ctatattaaa   40620
gtctcatttc ttatttgggg tgctagtaac acaggtatat tcagtttaat tgatagaact   40680
tttatatgta tgttatattc aataaaaagt tcaaaaactt tttaaaaata aaaattgtta   40740
aaactttgaa gcaaagatac agagaggaat aaaaagggtt actgaaaggt gaccttgggg   40800
agcagggaaa gactgggaac ccacacccttt ctgcagagag tcaatgtgga gcatctggtt   40860
tgcattttct ttttgcttct atatcacagg ctgaaactcg gttcagttat ttttaggagg   40920
cgaacaaagg tgcagcaaga acagagaaaa agtagtgact cacccgcaga gccatcgaat   40980
ccagagacaa aagcccgccg acagtcacat ggagcaatat actcactctg gaaaacaaag   41040
atgacaacaa agtgggcctc gatcagtcat gagcagactg ttctgcctgc ttagccttgt   41100
gctaggctca gcggggacta tgaagactgg ggaatccttg gccccgccc tcaagaagcc   41160 aacagtctag ctgaaaacaa cagattagca cacactgcag aagattgaat taattaaggg   41220
cagagagagc tgttcccttt agcctctatt tcctcattag gagaaccaaa gcacatcagg   41280
agaaacagat aaaaactgct ctttcttcac tgagatctta ctcaaaaatc aaaccaataa   41340
tagccttctc ccctccttgc cactgacatt taggcatctg ttattttct gaaaagtaag   41400 gctgaatttc tgtgttaagc accaacaatt ccctaactta agtttctgta gatactgact   41460
tgtttccaaa cttcctgttt gggtcctcct ctgaggtagc atcaccaatc tctcccatgc   41520
agaccctgtc ccttcctgct acagagtgag cggaaacgct tcatccaatc caggaggctt   41580
cagcaaaata aaatgtcatg tccaaaacca aggtcttctc agctgataat ccccttgcct   41640
ctgtatggaa ggggttaggg agtgaagaaa gtaagaaatt cttacgcgtg ggcaaagggt   41700
acaagtcaaa gtgtgcaact tctggtaata gccagtgagg cacagagagt ttaagtaact   41760
tgccccaaat cacacagcta attaagtagc agaggcagga tttgaaccta agcagtcaac   41820
tccagagtct ggactctgaa gccctatgcc aggctgccaa tgcatgacac tttatctctc   41880
```

```
gccctcatca ctctctagga taagaccaat agcaaatgag aaaactgagg ttcaaagaga    41940
gaatctttaa gtaagctgcc cacttacaag ttaatagtag gtcaggatcc aaagccaggc    42000
ctgcctgagt acagagctgc tgctccttct gcagttacca ggattctccc aagccaaagg    42060
acctggcaag gttaagaaag tttagggtgg ggaatggggc tgctggccag acccaaggca    42120
tttttaggac agtcaacatg atgtaggggg aaaaggccct catgttcctt tcctgctata    42180
tggttaagaa ctacccctt cagccaggca cagtggctca tgcctgtaat cctagcactt    42240
tgggcggctg aggtgggagg actgcttgag cccaggaact cgagaccagc ctgggagcat    42300
ggtgaaacct catgtctaca aaaatacaa taattagcca ggcatggtgg cacgtgcctg    42360
tagtcccagc tatttaggag gctgaggtgg gaggataatc tgagcccggg aggttgaggc    42420
tgcacagtga ggcatgattg tgccactgta ttccagccta gcaacagag tgagaccttg    42480 tctcaaaaaa ttaaaacaaa aattaaaaaa aaaaaaaaa aggactgcct ctttcaccaa    42540
ggcaccggca atcacagcct caaaccagcc tccaggagaa tactagaagg gccagcatag    42600
agaaccacaa tggcaggata aagcagctct gggccacctg cccactagcc caggcccagc    42660
tgcatagtct gcaacaagtc ctggcagctc tctcagcctc atttcctcat ctctaagaca    42720
ggtcatttca gattgctaaa tgcaacagca agcacgtttt attcctaaag cataagaac     42780 attcggtcaa cagcactaag gaaatagaaa gaaatggcca ccagcatcgt ttaggaactg    42840
cagaatcctc acttgtttat taaccgagta attactgtgt gcaagacttt ttattaaaaa    42900
gtaacaacgg ggggaagggt ggcccacaca tctcctagga ctcttgtgag aaacagtaag    42960
ttaatgtctt tcaaaactca ccagaaactt gaaagtgctg cacatatgca atggaagaga    43020
tattattaat ctcttcttcc taaacagtga gaagacatct aagggggctgg gaaaactaag   43080 ttaaaaataa ctcttgtgct aaaaatcact gcgcacaatg gggaatacac agtgagggca    43140
ctctccacca acatgacgcc acaggcttgg ggctcttcca cccgtgacac agggtgaaga    43200
tactggcaaa gactggcaga gaatgcagtg caggtctgag cccggctgga ctcttccatt    43260
cagggacata gtactctagg gatgccccac ccctttctgg gcaagcttgg gagagatgga    43320
agatccgcag ggtttaccta gacttctcca tcagcaaagg caaggaaaga gttcctccaa    43380
agggaggtgg aattaacagc aaatggacat gtttagtttg ggatggagac aaggtctggg    43440
gtaagaatgt ccagacatga cctaagtggt caacattcca gaaagacatt gctaagcaag    43500
gctggccaca gcctcacctc cacactgaca ggctatgcag aagccagaca agcactgggc    43560
ccagggctgt cactctcctt ctcccaggca tgaagctggc aacgcccagg ggcggtctcc    43620
ttagaacaca gcatagggcc taaaataaac caaagctgta gcatgctagg aaaaaggcac    43680
aaagaagcac agctgctggc ttttctcaa aaccaccac ttctctccat ttctaatagc     43740
agcactcagt ccaagcctcc atcatctcta cctggactac cgcccctaca atccactctg    43800
cacatacact cagagtgagc ttttccaaat atctaagatc atgttagcaa cctccttaaa    43860
accctccaat ggcttcctat tatatttaag ataaaatcca aactctggcc cagtcaaggt    43920
accagctgat gtgactttgc cagtcctctt gcagctctgc tcccattcac catgctccag    43980
acacacccac ctccttttg ctctttgcat atcctaagct caatcctgcc tcaaggcctt    44040
ggcacatgtg cttccatgtg cctataaaag tatttctgat catggtaagg ttaggtcctt    44100
ctaatcatta cattgtgaga tcaaatatca cctctacaga gaggcctacc tgtactaccc    44160
agctataata gccacctggc cacttttaag tctctgtata gcacacacat actctagata    44220
tttgtctttt ttttttttt tttcttttgg agacaggatc gccttctgtt accctagcta    44280
```

-continued

```
gagtgtggtg acacaattat ggctcattgt atccttgacc tgtcaggttc aagcaatcct     44340
cccacctcaa tcttctcaat agctgggact acagcaggca cacaccttt ttttttttt     44400 ttttgtagaa acggggtttt accacgttgc caggctggcc ttgaacttct gggctcaagt     44460
gatcagcctg cctcagcctc ccaaagtgct aggattacag gcaagagcca ccatgctggg     44520
caatgtttct cttcttaatg aacttttat atgtttattg gcttgttcct caaccccat     44580 cttaacccca agcatataag ttccatgaga tcagggtatc tgtcctgtcc ctgcactcag     44640
cacaggtgac tagatcctca acccacattt gtattataaa tgaacaagca gaaagagaca     44700
tgaagctttt ccctacatcc agttaaaacc tcaaccatat ctacgaagat ggacgaaggg     44760
accatgagcc aaggaatgca ggtggcctcc agaaactgga aaaggcaagg aaatggactc     44820
tccctggagc ctgcagaagt aacatagccc tgctgaccca ttttagactt cagacttcca     44880
gaaccataag agaataaatt tgttttaagt cactgtggta atttgttata gcagtgatag     44940
gaaactaata cattatctaa tggggaaaag atcgtaaggg attataaatg gggtttcaaa     45000
ttcaaatacc tcagggtaca ggacaaagga tatcttttct aaagacagca gctcctactc     45060
agctctgatt tctgaaatgc aggccacatg ttgctaacct tcaatatttc agaagaagcc     45120
agaaatatgg gttcatgaga aattacccaa ttttttaaatg ttggcatcta attccaacaa     45180
tataaacaat acatagccaa ataaagcatc tgtaaactac aaaaaaaaaa aaagctagtc     45240
atctctcaaa aatctggttc aagtgctccc ttttccatga agcttcctga cccacttcag     45300 cttttcagagg ctcccacatt tctgaatttt acaggaccat ccatgttggc acttatccat     45360
accctacctt ggataatgct gacaaataat gttagctaag attatttagt ctgtattgtt     45420
tattattgtc tcaacaccta ctagtcaata actgtattca tttcctctca ttctaatcct     45480
cacagcagcc ctggaaggta tcatccctcg ctaatctaca gatgaaaaaa atgaagctta     45540
gagaaataac taacttcccc aagtaacac cacagtaaat ggcagaacca agatctgaac     45600
tcaggtctga cttttttttt ttttaagatg gggtcttgct ttgtcgcctg ggctggagtg     45660
cagtggcgca atctaggctc actacaacct ccacctccca ggttcacgcg attctcatgc     45720
ctcagtctcc caagtagctg ggattacagg cgcccaccac cacacccagc taattttgg t     45780 attttagta gagacagggt tttgccatgt tggtcaggct ggtctcgaac tcctgacctc     45840
aagtgatccg cctgcctcga cctcccaaag tgctgggatt atggacatga gccactgcac     45900
ccagcctcag gtctgactt cgaaagccca tacccttgca agctgccaag caacctcttc     45960
tacttttgta cagaagttgt acacatctag tctcacaatt ggattataaa ttctgaggga     46020
acaaggaata cgaggtgtat gctgcactta cctctacttt catcagccac agaatagaca     46080
tctcctacaa ccagcagtta gaactctgtt caagcctggt tccccactta ctagctgggt     46140
gaacctgggg ctcaacttcc tcatctgtaa aatggggatg aacataatgc ccaccttgaa     46200
gggttgaggt gtgacataaa gcaattagcg catgccgaac atctgatgaa ctgcagcact     46260
tattgctatg aactgcaccg agcttgactc tatagcaaac ataagaaact atcttctcga     46320
agtggacaat cggcaatagt agacagatat tccatgaaat attaacacta ataaacagcc     46380
atataaacga tgctgaacat gcagtgtggt atttgctata gtttaaagga tgctcagatg     46440
tgccttagat ccatcagacc aagctcagag gtttgactgg gccaccaagg ataggcgaag     46500
agagcaggaa aacagtccag agggaaaggt gtgacaaggc ccagaagcaa gaggcaagag     46560
gcctgtcatg aggcgacacc caattagcct aatggcaggg gcaagaagtt caaggagca     46620
```

-continued

```
gctgcagaga tttctgtaaa ggccgtctga agacaaatag tcaaagacct caaacaccag    46680
actaagaggc ttgaactttta tcctgcaagt tctagagaga cactaaaagt tgaagagagg    46740
gtggtgacat gaccagagct gggttttaag aagagggatc aacatggctg gtcacatgcc    46800
gatggaactt gccaagtaaa gctgacagct gactgccaag ataagcatga ctaaagttac    46860
tagagtccac attagcgtga catctttccc cttccctgac cctcttctcc catcagccat    46920
gagcttggca ctgtgcctca aatatacaag gttctcaaga aaattgaaac tgaatgaata    46980
aatggccatc ggtccacagg aagtaccaaa agttagactg tgaatggaga tgtggactcc    47040
ttgtttccaa atataagtta ttggcatttt tttctctcct aaatgaaacc aagtcagggt    47100
atgtgggaaa aactgacagt tgtccaaaga tttgtgctcc ttccttagtg tagaagagtc    47160
actgaaaagt agctgcccag ccaggccttc attcccatgc ctcattacat tgaggtgagg    47220
tcacatgact tattcttacc aatgaaatgt gggtgagagg tgatacctgg gtcggggctc    47280
taacaaatga gtgtgccctg tccatactct gtccccttcc accagctaaa atggtggtac    47340
tatgggatgg aagagcctag atccctgaat cactttccct caaggtagag ggaagtcccc    47400
caccaaccag gaacacccac tctatactgc tacatgaaat aagaaataag gctttacaat    47460
accaggccac tgaaacttcg agatgtgtta ccacagctag cattattcta acacaacaga    47520
taaaatcact gtgggataaa aatcattaac cccaccccaa gagaaagcct gtttatgaaa    47580
tacaaaacaa aacaggaagc tgactccagg agaatggagt agggtccaaa gagtttagga    47640
aaatctgaat catgtcttcc aggaggagga accacaaaca aagccaaaaa ttcacattgg    47700
cagagtcagt ccctgacaaa acatcaccct ttgactaagc caagcccaac aacataatat    47760
ggggtctacg gatgaggagg atgaggaatc aagatttcta aaaggcagtg ctggcacagc    47820
tctgactcca accaaggatt ctcctgcttt gaggcaagtg gtgcccacga atcccaatat    47880
acgactagga tggtacatga aagtatccag attaccagag agaacagacg attccttgct    47940
ataaaagtcc cccagggccc aagctcatta atacaacaac cctaatacca caacccttgc    48000
tctgagttta aaaagaagaa acccttagag ttgcagagga cagagagaag cagaccactg    48060
cagtgccaag tccttgcgta attatgcatt tgaggtacgt tttctctctt gcagggaaca    48120
gcgtgtgggt gtgtatattt gtgttttgga aagtacacaa aggacagaat tcaagattcc    48180
ccttcacttc tccaacaccc tcccctcccc agccgtagga gaaactccat caacccagaa    48240
tctaccctga aatgaaacaa ttaggaacaa gagccacagg gaacagcagc ctctctatta    48300
ctgaggaggc tactatggca ggtcacacat gaagccagcc cttccttctt gttctcacaa    48360
tcacagcaag gatccagagt cccacttaac agagtcgccc caactatgtg gctcttctcc    48420
acaggaacta aaacaaggaa cccatttcct tctgttgatg gcaccacaaa cactcccagg    48480
cttcaaacct tcccaatccc ctctaccacc tgcctgcaag gtccacattt aatccaggtt    48540
gtactacttc tccaaatcct accctcctc tccgctccta accccagtac ccaagtccag    48600 gccctctta ccccaactct gagatcctgc aaggcctaac aggtttctca attcccagag    48660 tctccttct ccaacccata ctaaacactg ctccctctga tcatgtcact ctaaaatcct    48720
gattctggtg gtcaaggaca accatgacca gtcagggta attcatggat ggtcttaacc    48780
aggccactgt tctcccttct tcaagcttat tgtcatgcat gttctcctaa ttccatagat    48840
acccatggta tttcttacca tttgatccag ccatcctatt actgggtata tacccaaagg    48900
attataaatc atgctgctat aaagacacat gcacacatat gttttattgcg gcactattca    48960 caatagcaaa gacttggaac caacccaaat gtccatcagt gatagactgg attcagaaaa    49020
```

-continued

```
tgtggcacat atacaccatg gaattctatg cagccataaa aaaggatgag tttatgtcct  49080
ttgtagggac atggatgaag ctggaaacca tcattctgag caaactatcg caaggacaga  49140
aaaccaaaca ccgcatgttc tcactcacag gtggcaactg aacaatggaa catcacacac  49200
tggggcctgt catggggtgg ggggagggg gagggatagc attaggagat atacctaatg  49260
taaatgatga gttaatgggt gcagcacacc aacatggcac atgtatacat atgttaacaa  49320
acctgcacgt tgtgctcatg taccctagaa cttaaagtat aatttaaaaa aagatttcca  49380
tggtatttct tgtacttctc tccctctttc catgcatcca aattctacct gttcacgttc  49440
caatttaaat cctactttct ccatgaagac ttccctgatc ctgccagctt aaaatactct  49500
gtcacctttg aattcagttc cactttaag taaacttaca ttacagttgc caccagccac  49560
atgtgtctaa gcacttgaaa tgtggctatt gtgactgaga aacagaatac ttaattttat  49620
ttcactttaa taaattgaaa tacaaattta aaaactgata ttcaagattc agttactgga  49680
aaacttctaa gtatgtttag aacaacttgg gtacgtgagt ccacctttc aactgtcagt  49740 cttatgaaat ctaaacacag atcaaatatt tccaatgaaa atttcacatt caaattgcga  49800
agttttgtaa atgtaaaaac ttcccatatt tgaaaccaca gcataaaaag gaatgtaaag  49860
tatcttctta ataattttta taatgatgat gtgctaaaat aatattttgg atatgttgga  49920
ttaatatatt gttaaaatta atttcactgc tcttttactt taatgtgtct atgagaacat  49980
tgaatattac atgtgtatct cacagattct acttagacag tgctaatgag gtcctttccc  50040
atgacattca ccagtttctt tttgtgttct catttatgac tgtggcttac ctattattta  50100
atctcttcaa agggaatctc attcatctcc acaacagtaa taacaacaat agcggcagct  50160
aatatgacga gacttttcaa gtgacatcaa gcattcaagc agcaagcatt caagtgcttc  50220
aagcattcac atctacagta tgaacccatt tcatcctaac aatagcccat gcggtacata  50280
ccacactgtc acaatctcct ttttgcgaat gcagaaactg agacccagaa agtttaattg  50340
acacttcaga atttcatgta acttgcctga tgtcaagcaa ctagtaagta gcaaatctgg  50400
catctgaacc cagagaggct ctagagctca tacgcttacc tatatgctaa ctacctgccc  50460
tctgcatttg ccccagacct agccctgagc agcagtcaga aaacatgcaa acaaacaaaa  50520
cacaatttct ccacgtatgt aagacagaca gctaagctac agcaatagaa atgacagtta  50580
agattataaa agaaagagtg gagagggtg atgaagatgg aaggacagca agagtgcaaa  50640
aatgtaagtc tgtgaagtct aaacagtgac ttctgcaata agagcaacag ctaacaccaa  50700
gcaagcttga tacattttgt attttcagga tgttgctaca aaacacatct gtctcagatt  50760
agagcctcag tttcctcatg gagggaaaag ccatctaatt ctgatattgc aggatcatta  50820
gtaggagata aagagctgag ggaaagcctg gaacatcccc tgtggcttag atggcctcac  50880
tgccactccc agaaggaatt gcttcgggtg taataggcca cacctactgt caaagataga  50940
acatttttaa gtatcagtca gggtgtccaa aaatcagctt tatgatgacc aaacaaacaa  51000
aaaaagctgg caaggaaca gcacccagga ccaagaacat caagataaac ttgactcagc  51060
tataagatgt cggtgtctcc tactagtaaa cacacagata atatcctaac tccaggcaaa  51120
agaaaactga aattgaaata caaacactac aaagcttcca acacacccttt aaccagaaac  51180 cttcaactct taattcaagt aacattagca ggtcgaatct ttctgtacac tgaggcctcc  51240
cctggaggta aagattcaca aatagtagag ctattaggag tcttcagctg aggctccatg  51300
acgacctgtg agaacccttt cggaggaggg ccccaatttc agcaactgt gccaggggac  51360
```

```
ttacagaact gcccaaacca actgctacat aatcatcatg tgctccagtt gcgggaacca   51420
ccatctgctc aacactaaca gggtgactgc aatcaaatca gcctagggca actgtccaat   51480
gcttgaaggg cagaaaatta aaaatgccac tggtgaatcc agcagagaat ccaggtgaca   51540
tgaagcccac atccaaaggc tgaggcctag gactgacagg aaacaaggaa gagctcatca   51600
gaggggccca agaaaagaa aaaacaaaat tccttgaaga caaggcaatg gtctgccctt    51660
cttaaatggg ggagtgccca gctcctctgc tacctacgac tcataccata actcaggctc   51720
aaatcacagt ggccagccta cttcctcacc cagtccttgg tcaagatgat attttgcttc   51780
atatgaagtt ggtcaatctt ttttttttt tttttgagac agggtcttgc tctgttgcct    51840
aggctggagt gcagtggcgc aatctcagct cactgcaacc tccacctcct gggttcaagc   51900
gattctccca ccacagcctc ccaagtactc aggactacag ccatgagcca ccacgcccag   51960 ctaattttg tattttttgg cagagatggg gtttcacatg ttgaccagcc tggtttcgaa    52020
ctcctgacct caggtgatcc acctgcctca accttccaaa atgctcggat tacaggcgtg   52080
agccaccaca cccagcctga agttgaccaa tcttatttgt ctattctaat gaacacaaac   52140
gaacctcacc aagtctatcc ttaccttccc actgcctact agatctaaca gttatgcacc   52200
cagcctcatg gcttcctcac atgccaccac cccgattcca gcttgatatt ctacttttcc   52260
tatattctgc caggctgaac agccagtgag ctggtgcctg aatacacctc tcactctgac   52320
ctctcccttc atccacctct acatgcaaga cccatcatcg gatgaaaagt actatcacag   52380
aacaacatat aaaggtattc catgaaacac tagagtctcc cacccgccc ctgaaataac    52440 tgggaaaatt ccatggacat ttaagtctga aaatgctga atactttatc ccctccttag    52500
aggtacagag tgcacatcag catattaaag gccctgagaa gtcctgcagc tatgaaactc   52560 attgggcaa aggacttgaa tagacatttt ctccaaagaa aatatacaaa tgggaccaaa    52620
aagcatatga aaagatactc aacatcacta accatcaggt aatgcaaatc aaatctacaa   52680
tgagccatca cctcacaaca aaacaaaaaa tagcaagtgt tggtgaggaa gtggaagaac   52740
tggaatgctg tgtaccattg gtgggaatgc aaaatagtac aggtgctgca gaaaacagta   52800
tggaagttcc cccaaaaatt aaaaatagaa ggatcatatg atctggcaat ctcacttgtg   52860
ggcatatatc caaagaatg gaaaacagga tctcaaaaag atacttgcaa acccatgttc    52920
attgcaacat tactcacaat agccaagagg tggaaaaaac tgaaatgacc atccacagat   52980
gaacaggtta aaaaaaaaa gtctctaaat aaaatggaat attattcagc cttataaaag    53040
aaagaaatcc tgtcatatgt tacaacatgg atgaaccttg gacactatac taagtgaaat   53100
aagccagtca caaaaagaca aatactgcat gattccaatt acatgcgtta tctaaagcag   53160
gcaaactttt ttttttgaga cggaatctcg ctctgtcacc caggctggag tacagtgctg   53220
caatctcggc cggctcactg taacctccgc ctctcaggat caagcaaatt ctcctgcttc   53280
agcctcctga gcagagggat tacaggcacg tgctaccaag cctggctaat tttatattt    53340 ttagtagaga tggggtttca ccatgttggt caggctggtc tccaactcct gacctcatga   53400
tccgcctgcc tcggcctccc aaagtgctgg gattacaggc gtgagccacc gtgactggcc   53460
cagcaaaatc ttagagagag aaagtagaat ggtggttgcc agggatagga ggggaggaga   53520
gagactggga ggagctgttt aatggatata agtttcagt tttgcaagac gaaaagttc    53580 tagagatctg ttgcacaaca atatgtgcat gtagttaaca ctacagtatt gtacattttt   53640
aaatggttaa ataaatgtc atattataca ttttcacca caataaaaaa acactgttca     53700
gctcatttca ctattttctc aactaacaaa tatattttt gtagagcatc ttacaagaca    53760
```

```
caacaggaat actgaagaac acacacagtt tggggaacac tgttctaaac atcaaagtat    53820
cctaaacttc atactgttgc ctcaaatatc cgatcccttt gcttattcat ttcaagccct    53880
tcatttgctc ctaaggccag gaaatccatg tctccaggca gagatccaat cttgaggttg    53940
agttgttccc aggttaatac aggcctgacc ttgtcgcaac catgtagacc aggacctctg    54000
gggagaggca ggaagtcagc cagccagaat ggacatgttt tgtgatcttt gctcaactta    54060
cagaaatacc cttatctacc accccctcca tcatggtgga ctggtggacc cccattactc    54120
atgtctgaca tcacacagac acacacacag acacagacac gcacacgtgc acacacacag    54180
agtaaccagg accatgcaga accaagttgc tacatatacc aatcaagttc tcatcctgga    54240
cttttgaattt gggggattaa ggttctagtt caatctggta tcttgaaagt aagagaggaa    54300
aagatataaa tgtaggtgtt gtcaggttta tatgacccaa ccagttggct gaaaagaga    54360
aactgatatg cagcaagacc tgaaaaccct cccgtcccag ttcttcttga ggcctgcta    54420
cattcctgcc ctcatgttcc acaagacacc ctatctgagg ccctgacaca cataactctg    54480
agagcaccat tcacaatctg gagttgtgcc aatatggtgg ctctgcccct gaatccttat    54540
aaagcatttt tattgctcaa ggtatctcaa ggcagtttct attacctgca actgaagaat    54600
cctgtaacaa cagctttatt tcccaccact gcttttact tccctggtct cttgccaggg    54660
aaacctgtcc cactgtttct gaagagcatc cgaagcttcc ctgtttcttt gcctttgctg    54720
ccactaatac ttttacctag aacctctttc ctcctcctcc accccatccc tctatttacc    54780
caaactccac ccatccttca aggtccaatt caactgtctc ccctgtgcca tgaagctctt    54840
catcatcttc ccctctcacc ctcaaacttc cacagccttc tgtccagatt ttcttgatca    54900
cacttaccac attttacctt acaatacagg tatgtgcatg tacatctaaa ctccattatt    54960
aagctgtatg cttcttaaaa ccaggaacaa tcctcatctc tatatcatgt ctaatacctg    55020
agatgggtag ggccttatac ataagtaaag gctgggaaaa actgtactta tagatgattc    55080
tgtggaagaa tagcactctt atattatttc atctctcact aaaccataag cctagtgaga    55140
gcagacattc aaccttaagt tcatctttgc accctacagc accataacca cagtgtaagc    55200
actcaaacac ttgctgactc aatgacttca cagtggatcc tagaatcctt ttaccctacc    55260
gcccatcaac cctatcacat gaggtctctg cctctccaac tctcctggat tgggcaaaag    55320
agagacaggg caaacaattc tgctaggaac acagtgtggc agaggagatg tggagtatgc    55380
cagcaacaga aagttccaga acttctgtcc cttaatttgc ccactaattc ttcattgaaa    55440
gatggctaag tcactggaat caaggaagct agggccaatc cacaagcatt cagtgagacc    55500
tattggacac agatccccat agcaagccct ggaagggctt ggttgtggcc ctggttgtgg    55560
gttgacaatt agaatcctac aaacacatta gggctgggga aaaagactg aaaagaaagg    55620
agaggcccat tgccatgcag tacctgatga gcatctcccg atgggatgat gtaggcctgg    55680
atcggttcgg tcacatactc agagttcctc atggcttgtc tcagctgccg aagcagctct    55740
gaagtcacct ttggaggcat tctgccgtct gcaacaacag gagagcaaat ttcaaaacca    55800
gcctgccccc agcaattcaa cgtccagttc gaagtgggcc acagagagaa gtgccttcta    55860
cgttctgccc cactcccagt taggtcttca aattgatcac tccaccacca gaccaagacc    55920
aaagctgcca gaaacactaa tgttcacagt tcttaaatac tacctccaaa tagccatttg    55980
tggccagaaa agttcagcta ctaaccattt ccaacttgac tggttacctc tttcactcct    56040
aggactttat tcaagaatag gagataagta cacagaaatt taggtgttta tctttgttta    56100
```

```
tagtagaaaa aagcaggaga agtgtatggt cagttaaata aactataata cgtacaacag    56160
tatactgtgt actcattaaa aattacacag acctagaaaa gaattacata gacttatata    56220
tttgatttgg aaagatacct agacaacatt tgtgggtgat taaaaacaga tgacaggctg    56280
ggcgcagtgg ctcacgcctt taattccagc actttgggag gccaaagcag gcagatcaca    56340
aggtcgggag atcgagacca tcctggccaa tatggtgaaa ccccgtctct acaaaatata    56400
aaaaatcagc caggtgtggt ggcacgtgcc tgtagtccca gctactccgg aggctgaggc    56460 agggaatca cttgcactca ggaggtggag gttgcagtga cctgagacca caccactgca    56520
ctccagcctg gcaaaagacc aagactccgt ctcaaaaaac aaaacaaaac aaacagatga    56580
caaaggaaaa aaatatagat tgttcttatt tatttaaaat tgtgtatgta tatatgcaaa    56640
gagaagtttc tagaaggaca gtcacccaag tgttaagagt ggttaccttt gggtaagtaa    56700
atttggagta attattgtct tcttgtattt ttctgctttt taaatttgac tgctttaaaa    56760
gagtatgttt tataaacctt ttgttaaata tccagctaca gatttagaga agaaagttcc    56820
gtccactagg agtcaaaagt cttatcttct agtgaatacc tgctaccaac cagctgtgca    56880
agggagaagg ggaccagggc ctcaatgctc tgtgttctcc tctttaaagt atggcgggag    56940
tggccgggtg cggtggctca cacctgtaat cccagcactt tgggaggcca agcaggcgg    57000 accacaaggt caggagatcg agaccatcct ggctaacatg gtgaagcccc gtctctacta    57060
aaaatacaaa aaagttagcc aggcgtggtg gcgggtgcct gtagtcccag ctactcagga    57120
ggctgaggca ggagaatggc gtgaacccgg gaggcagagc ttgcagtgag ccaggattgc    57180
accactacac tccagcctgg gcaacagagt gagactctgt ctcaaaaaaa taaataaata    57240
aagtatggcg ggagtggatg agacccaagg ttttcaaacg aagtcccaag gctccagggg    57300
agtctaccat tcaaataaaa ccagagttgg aatcaccagc tttagaaaat acaaaatagg    57360
aatagaaata taaaactaat taaaatgaaa tgttaaagat gttaactctg gtcctactag    57420
aaattcttaa acttgtttca tctatatcta tagtcaggaa tagtctcttg tactcactta    57480
gtggaagcac agatgataca agctgactta accactttag ttggttcttc aaaaagacct    57540
tttctcaaca atcactgata ttagttaatg ttctgataaa catcatagct gtagtcctat    57600
gtctacataa caaaacaact tcagaaggag ccaattacag aatagtgatc atgcatattt    57660
cactatatcc catatactgg cacaaaacta tactattaga attcaaagta gaataatgag    57720 ttttttccaac tcatttttaa tagacttcat tttttacagc agttatagtt tcacagcaaa    57780
actgagcaga aaatacagag ttcccatgta gctccagccc caacacacac acagccccct    57840
gccactatct gcatccccaa ccagagtagt acatttgtta aaatggatta acttacatta    57900
acacatcatc atcaccctag gtccacagct tactcctgca ttcattcgtg gtgttgtaca    57960
ttctatgggt tttgaaaaat gtgtaatggc atgtatccac cattatagta tcacacagag    58020
tactttcact gccctgaaaa ttctatatgc acatgcagcc tattcattcc tccttcctcc    58080
tctcctctaa cccgacaata actgagcttt tctactgtct ccatagtttt gcctgttcta    58140
taatgtcata cagttagaaa cattctacac agagcttttg ccagattgat ttcgttctac    58200
ttaaagaata atgcatttaa gccaggcgca gtggctcaca cctgtgtgcc cagcgttaag    58260
```

```
                                          -continued gccaaggcta gtggatcacc tgaggttggg agctcaagac cagcctgacc aacatagaga    58320
aaccccatct ctactaaaaa tacaaaatta gctgggcatg gtggcacatg tctgtaatcc    58380
tagctactca ggaggctgag gcaggagaat tgctcgaaca caggaagcag aggttgtggt    58440
gagccgagat cacaccattg cactccagcc tgggcaacaa aagcgaaact ctgtctcaaa    58500
aaaaaaaaaa aaagacaata tgcatttaag gttcctctat gtcttttgat tgcttgatag    58560 ctcattttttt tagccctgaa taatactcca ttgtctggat gtaccaccat ttatccattc    58620
acctgctgag ggacatattg gttgtttcca ggttctggta atcatgaata aagctgctat    58680
aaacatctgt gtgcaggttt taggtggacg taagattcca actcatttgg ttttt          58735
```

US 7,273,718 B1

ISOLATED GENOMIC POLYNUCLEOTIDE FRAGMENTS FROM CHROMOSOME 10Q25.3 THAT ENCODE HUMAN SOLUBLE AMINOPEPTIDASE P

PRIORITY CLAIM

This application claims priority to provisional application Ser. No. 60/386,941, filed Jun. 7, 2002 under 35 U.S.C. 119(e), the contents of which are incorporated herein by reference.

FIELD OF THE INVENTION

The invention is directed to isolated genomic polynucleotide fragments that encode human soluble (cytosolic) aminopeptidase P, vectors and hosts containing these fragments and fragments hybridizing to noncoding regions as well as antisense oligonucleotides to these fragments. The invention is further directed to methods of using these fragments to obtain human soluble aminopeptidase P and to diagnose, treat, prevent and/or ameliorate a pathological disorder.

BACKGROUND OF THE INVENTION

Chromosome 10 contains genes encoding, for example, the alpha-2A-adrenergic receptor, the beta-1-adrenergic receptor, glyceryl-3-phosphate acyltransferase and G protein-coupled receptor kinase-5. Recently, it has been shown that the soluble (cytosolic) aminopeptidase P gene (XPN-PEP1) is disposed at 10q25.3 (Sprinkle et al. Arch. Biochem. Biophys. 378: 51–6, 2000), a gene discussed in further detail below.

Human Soluble Aminopeptidase P

Human soluble aminopeptidase P, an aminoacylprolyl peptidyl hydrolase, catalyzes the removal of the N-terminal amino acid from peptides in which the second residue is proline. It is believed to act physiologically by degrading peptide hormones such as bradykinin and substance P. It may also degrade collagen-related peptides that have N-terminal sequences of the type Xaa-Pro-Hyp-. A functionally-related enzyme is membrane-bound aminopeptidase P, the gene for which (XPNPEP2) is disposed at chromosome Xq25 (Sprinkle et al, Genomics 50: 114–6, 1998). The membrane-bound enzyme is disposed, via a glycosylphosphatidylinositol lipid anchor, as an ectoenzyme on endothelia and epithelia. Soluble aminopeptidase P is disposed intracellularly in virtually all cell types, including astrocytes, lymphocytes, platelets and chromaffin cells.

OBJECTS OF THE INVENTION

Although cDNA encoding the above-disclosed protein, soluble aminopeptidase P, has been isolated (e.g. see accession no. AF195530), its exact location on chromosome 10q25.3 and exon/intron/regulatory organization have not been determined. Furthermore, genomic DNA encoding the polypeptide has not been isolated. Noncoding sequences play a significant role in regulating the expression of polypeptides as well as the processing of RNA encoding these polypeptides.

There is clearly a need for obtaining genomic polynucleotide sequences encoding the soluble aminopeptidase P polypeptide. Therefore, it is an object of the invention to isolate such genomic polynucleotide sequences.

There is also a need to develop means for identifying mutations, duplications, translocations, polysomies and mosaicism as may affect the soluble aminopeptidase P gene.

SUMMARY OF THE INVENTION

The invention is directed to an isolated genomic polynucleotide, said polynucleotide obtainable from human chromosome 10 having a nucleotide sequence at least 95% identical to a sequence selected from the group consisting of:
  (a) a polynucleotide encoding human soluble aminopeptidase P depicted in SEQ ID NO:1;
  (b) a polynucleotide consisting of SEQ ID NO:2, which encodes human soluble aminopeptidase P depicted in SEQ ID NO:1;
  (c) a polynucleotide which is a variant of SEQ ID NO:2;
  (d) a polynucleotide which is an allelic variant of SEQ ID NO:2;
  (e) a polynucleotide which encodes a variant of SEQ ID NO:1;
  (f) a polynucleotide which hybridizes to any one of the polynucleotides specified in (a)–(e) and
a polynucleotide that is a reverse complement to the polynucleotides specified in (a) to (f) as well as nucleic acid constructs, expression vectors and host cells containing these polynucleotide sequences.

The polynucleotides of the present invention may be used to modulate human soluble aminopeptidase P levels in subjects (e.g., human patients) in need thereof and thus for the manufacture of a gene therapy for the prevention, treatment or amelioration of a medical condition by adding an amount of a composition comprising said polynucleotide effective to prevent, treat or ameliorate said medical condition.

The invention is further directed to obtaining human soluble aminopeptidase P or variant thereof by
  (a) culturing host cells comprising these sequences under conditions that provide for the expression of said polypeptide and
  (b) recovering said expressed polypeptide.

The polypeptides obtained may be used to produce antibodies by
  (a) optionally conjugating said polypeptide to a carrier protein;
  (b) immunizing a host animal with said polypeptide or peptide-carrier protein conjugate of step (b) with an adjuvant and
  (c) obtaining antibody from said immunized host animal.

The invention is further directed to a nucleic acid molecule including but not limited to a polynucleotide fragment, antisense oligonucleotide or antisense mimetic comprising a sequence of nucleotides which specifically hybridizes to noncoding regions of said polynucleotide sequences of SEQ ID NO:2 (human soluble aminopeptidase P). These sequences may be used to modulate levels of human soluble aminopeptidase P in a subject in need thereof and specifically for the manufacture of a medicament for prevention, treatment or amelioration of a medical condition. As defined herein, a "polynucleotide fragment" may be a nucleic acid molecule including DNA, RNA and analogs thereof including protein nucleic acids and mixtures thereof and may include a probe and primer. Such molecules are generally of a length such that they are statistically unique in the genome of interest. Generally, for a probe or primer to be unique in the human genome, it contains at least 14 to 16 contiguous nucleotides of a sequence complementary to or identical to a target sequence of interest. These polynucleotide fragments can be 20, 30, 50, 100, 150, 500, 600, 1000, 2000 or more nucleic acids long. Probes and primers may also be referred to as oligonucleotides. As defined herein, an "antisense oligonucleotide" is a molecule encoding a sequence complementary to at least a portion of an RNA molecule. The sequence is sufficiently complementary to be able to hybridize with the RNA, preferably under moderate or high stringency conditions to form a stable duplex or triplex.

The invention is further directed to kits comprising these polynucleotides and kits comprising these sequences. In a specific embodiment, the sequence(s) are attached to a substrate. In a specific embodiment, the support is a microarray. The microarray may contain a plurality of sequences hybridizing to non-coding sequences. As defined herein, a "plurality" of sequences is two or more sequences. Alternatively, the microarray comprises non-coding sequences as well as coding sequences.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to detect a pathological condition or susceptibility to a pathological condition in a subject comprising
  (a) isolating genomic DNA from said subject;
  (b) detecting the presence or absence of a variant in said genomic DNA using a probe or primer derived from a polynucleotide hybridizing to non-coding region(s) of said human aminopeptidase P; and
  (c) diagnosing a pathological condition or susceptibility to a pathological condition based on the presence or absence of said variant.

Probes or primers derived from SEQ ID NO:2 (human soluble aminopeptidase P) may be used to identify variants including but not limited to mutations, duplications, translocations, polysomies and mosaicism on the human soluble aminopeptidase P gene and may be used to identify patients with or having a propensity for conditions in which bradykinin or substance P is produced in excess, e.g., inherited angioedema or acute pancreatitis.

DETAILED DESCRIPTION OF THE INVENTION

The invention is directed to isolated genomic polynucleotide fragments that encode human soluble aminopeptidase P, which in a specific embodiment is the human soluble aminopeptidase P gene, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein, "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand. The human soluble aminopeptidase P gene is 58735 base pairs in length and contains 19 exons (see Table 1 below for location of exons). As will be discussed in further detail below, the gene is situated in genomic clones AL133416 and AL354951.

The polynucleotides of the invention have at least a 95% identity and may have a 96%, 97%, 98% or 99% identity to the polynucleotides depicted in SEQ ID NO:2 as well as the polynucleotides in reverse sense orientation, or the polynucleotide sequences encoding the human soluble aminopeptidase P polypeptide depicted in SEQ ID NO:1.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are:

Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score.

This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237–245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NO: 2. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42 C, can be used, e.g., 5×SSC, 0.1% SDS, 0.25% milk, and no formamide; or 40% formamide, 5×SSC, 0.5% SDS). Moderate stringency hybridization conditions correspond to a higher temperature of 55 C, e.g., 40% formamide, with 5× or 6×SCC. High stringency hybridization conditions correspond to the highest temperature of 65 C, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NO:1 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human soluble aminopeptidase P gene. These include but are not limited to an intron, a 5'-non-coding region, a 3'-non-coding region and splice junctions (see Table 1), as well as transcription factor binding sites (see Table 2). The polynucleotide fragments may be a short polynucleotide fragment which is between about 20 nucleotides to about 50 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600, 2000 or about 5000 nucleotides in length may be used.

TABLE 1

Exon/Intron Regions of the Human Soluble Aminopeptidase P gene (reverse strand coding).

| Exons | Nucleotide no. (stop codon 12803–5) | Peptide amino acid no. |
| --- | --- | --- |
| 19 | 12806–12931 | 623–582 |
| 18 | 16233–16331 | 581–549 |
| 17 | 17572–17649 | 548–523 |
| 16 | 18351–18524 | 522–465 |
| 15 | 19412–19480 | 464–442 |
| 14 | 20986–21045 | 441–422 |
| 13 | 23147–23218 | 421–398 |
| 12 | 25409–25489 | 397–371 |

TABLE 1-continued

Exon/Intron Regions of the Human Soluble Aminopeptidase P gene (reverse strand coding).

| Exons | Nucleotide no. (stop codon 12803–5) | Peptide amino acid no. |
| --- | --- | --- |
| 11 | 25622–25678 | 370–352 |
| 10 | 28129–28179 | 351–335 |
| 9 | 28783–28872 | 334–305 |
| 8 | 30373–30582 | 304–235 |
| 7 | 32007–32087 | 234–208 |
| 6 | 34185–34283 | 207–175 |
| 5 | 36003–36146 | 174–127 |
| 4 | 36457–36549 | 126–96 |
| 3 | 39675–39779 | 95–61 |
| 2 | 40965–41030 | 60–39 |
| 1 | 55647–55760 | 38–1 |

TABLE 2

Transcription Factor Binding Sites of the Human Soluble Aminopeptidase P Gene.

| Sites | No. of Sites |
| --- | --- |
| AP1_C | 12 |
| AP4_Q5 | 15 |
| AP4_Q6 | 6 |
| DELTAEF1_019 | |
| GATA1_06 | 4 |
| GATA2_02 | 4 |
| GATA_C | 4 |
| LMO2COM_02 | 8 |
| LYF1_01 | 14 |
| MYOD_Q6 | 12 |
| MZF1_01 | 34 |
| NFAT_Q6 | 10 |
| NKX25_01 | 27 |
| S8_01 | 12 |
| SOX5_01 | 39 |
| TATA_C | 7 |
| TCF11_01 | 37 |
| USF_C | 18 |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50–200 nucleotides in length and specifically about 50, 100, 200, 500, 600, 1000, 2000 or 5000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome genomic clones of accession number AL133416 and AL354951 have been discovered to contain the human soluble aminopeptidase P gene by Genscan analysis (Burge et al., 1997, J. Mol. Biol. 268:78–94), BLAST2 and TBLASTN analysis (Altschul et al., 1997, Nucl. Acids Res. 25:3389–3402), in which the sequences of AL133416 and AL354951 were compared to the human soluble aminopeptidase P cDNA sequence, accession number AF195530

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of the gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683–1684).

Once the DNA fragments are generated, identification of the specific DNA fragment containing the desired human soluble aminopeptidase P gene may be accomplished in a number of ways. For example, if an amount of a portion of a human soluble aminopeptidase P gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NO:2. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous human soluble aminopeptidase P polynucleotide. However, in a preferred aspect, and as demonstrated experimentally herein, a nucleic acid encoding a polypeptide of the invention will hybridize to a nucleic acid derived from the polynucleotide sequence depicted in SEQ ID NO:2 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human soluble aminopeptidase P polypeptide.

A gene encoding human soluble aminopeptidase P polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human soluble aminopeptidase P gene (nucleotides 58735 of SEQ ID NO:2) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NO: 2 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Komaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American,* 1980, 242: 74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention. Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region, which codes for an amino acid sequence linked to the amino terminus of the polypeptide which can direct the encoded polypeptide into the cell's secretory pathway. The 5'-end of the coding sequence of the nucleic acid sequence may inherently contain a signal peptide coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109–137.

An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola lanuginosa* cellulase gene, or *Humicola lanuginosa* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5ʹ-phosphate decarboxylase), sC (sulfate adenyltransferase), trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al, 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian cell (e.g., human cell), an insect cell, a plant cell or a fungal cell. Mammalian host cells that could be used include but are not limited to human Hela, 293, H9 and Jurkat cells, mouse NIH3t3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470–1474. Suitable methods for transforming *Fusarium* species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, human soluble aminopeptidase P can be assayed by its ability to release the N-terminal arginine residue from bradykinin or the synthetic substrate Arg-Pro-Pro-benzylamide.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the human soluble aminopeptidase P polypeptide produced according to the method of the present invention may be used as an immunogen to generate any of these antibodies. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the human soluble aminopeptidase P polypeptide, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for the human soluble aminopeptidase P polypeptide together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce polypeptide-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for the human soluble aminopeptidase P polypeptide.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Substrate

In a specific embodiment, the polynucleotides of the present invention, particularly, the polynucleotide fragments or antisense nucleic acids hybridizing to non-coding regions of SEQ ID NO:2 may be attached to a substrate. A substrate may be solid or porous, planar or non-planar, unitary or distributed. The polynucleotide may be attached covalently or applied to a derivatized surface in a chaotropic agent that facilitates denaturation and adherence by presumed noncovalent interactions, or some combinations thereof.

In a more specific embodiment, the substrate is a microarray. "Microarray" as defined herein is a substrate-bound collection of a plurality nucleic acids, hybridization to each of the plurality of bound nucleic acids being separately detectable. The microarray may comprise a plurality of polynucleotides hybridizing to a non coding region of SEQ ID NO:2. Alternatively the microarray may comprise a polynucleotide(s) hybridizing to said non-coding region and/or coding regions of SEQ ID NO:2.

Uses of Polynucleotides

Diagnostics

Polynucleotide fragments containing noncoding regions of SEQ ID NO:2 may be used as probes for detecting variants from genomic nucleotide samples from a patient. The variants may be allelic variants or substitution, insertion or deletion nucleotide variants. Genomic DNA may be isolated from the patient. A mutation(s) may be detected by Southern blot analysis, specifically by hybridizing restriction digested genomic DNA to various probes between 10–500 nucleotides in length, preferably between 20–200 nucleotides in length, more preferably between 20–100 nucleotides in length and most preferably between 20–50 nucleotides in length and subjecting to agarose electrophoresis. Alternatively, these polynucleotides may be used as PCR primers between about 10–100 nucleotides in length and be used to amplify the genomic DNA isolated from the patients. Methods for performing primer-directed amplification (routine or long range PCR) are well known in the art (see, for example, PCR Basics: From Background to Bench, Springer Verlag (2000); Gelfand et al., (eds.), PCR Strategies, Academic Press (1998). Single base extension (see, for example, U.S. Pat. No. 6,004,744) may be used to detect SNPs. Additionally, primers may be obtained by routine or long range PCR that yield products containing contiguous intron(s)/exon sequence(s) and products containing more than one exon with intervening intron. The sequence of the amplified genomic DNA from the patient may be determined using methods known in the art. Such probes may be between 20–5000 nucleotides in length and may preferably be between 20–50 nucleotides in length.

Thus the invention is thus directed to kits comprising these polynucleotide probes. In a specific embodiment, these probes are labeled with a detectable substance.

In one embodiment, the probes are in solution. In another embodiment, the probes are attached to a substrate. In a specific embodiment, the probes are contained within a microarray and are separately detectable.

Antisense Oligonucleotides and Mimetics

The antisense oligonucleotides or mimetics of the present invention may be used to decrease levels of a polypeptide. For example, human soluble aminopeptidase P has been found to be associated with the inactivation of bradykinin, an antimitogenic agent. Therefore, the human soluble aminopeptidase P antisense oligonucleotides of the present invention could be used to inhibit cell growth and in particular, to treat vascular stenosis or restenosis.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human soluble aminopeptidase P inactivates bradykinin and substance P. Therefore, the human soluble aminopeptidase P gene may be used to modulate or prevent conditions in which bradykinin or substance P is produced in excess; notably in acquired or inherited angioedema or acute pancreatitis.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," Science, 247, 1465–1468, 1990; and Wolff, Jon A, "Human dystrophin expression in mdx mice after intramuscular injection of DNA constructs," Nature, 352, 815–818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN and LIPOFECTACE, which are formed of cationic lipids such as N-[1-(2,3 dioleyloxy)-propy1]-n, n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612–618 (1996); San et al., Human Gene Therapy 4:781–788 (1993); Senior et al., Biochemica et Biophysica Acta 1070:173–179 (1991); Kabanov and Kabanov, Bioconjugate Chem. 6:7–20 (1995); Remy et al., Bioconjugate Chem. 5:647–654 (1994); Behr, J-P., Bioconjugate Chem 5:382–389 (1994); Behr et al., Proc. Natl. Acad. Sci., USA 86:6982–6986 (1989); and Wyman et al., Biochem. 36:3008–3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4_spermidine cholestryl carbamate (GL-53) and 1-(N4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106: 181–183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated genomic polynucleotide, wherein said polynucleotide can be isolated from human chromosome 10 and is selected from the group consisting of:
   (a) a polynucleotide consisting of the nucleic acid sequence set forth in SEQ ID NO:2,
   (b) a polynucleotide consisting of the sequence of nucleotides from position 12803 to position 55760 of SEQ ID NO:2, and
   (c) a polynucleotide which is the complement of a polynucleotide of (a) or (b) and encodes a polypeptide having aminoacyl prolyl peptidyl hydrolase activity.

2. A composition comprising the polynucleotide of claim 1 and a carrier.

3. An expression vector comprising a polynucleotide consisting of the sequence of nucleotides from position 12803 to position 55760 of SEQ ID NO:2 or the complement thereof in operable linkage with a heterologous promoter.

4. A recombinant host cell comprising the expression vector of claim 3.

5. A method for obtaining a polypeptide having aminoacyl prolyl peptidyl hydrolase activity comprising
   (a) culturing the recombinant host cell of claim 4 under conditions that provide for the expression of said polypeptide, and
   (b) recovering said expressed polypeptide.

6. A method of identifying a nucleotide sequence variant of SEQ ID NO:2 or its complementary sequence comprising
   (a) isolating genomic DNA from a subject, and
   (b) determining the presence or absence of a nucleotide sequence variation in said genomic DNA by comparing the nucleotide sequence of SEQ ID NO:2 with the nucleotide sequence of the isolated genomic DNA and establishing if and where a difference occurs between the two nucleotide sequences thereby identifying a nucleotide sequence variant of SEQ ID NO:2.

7. The method according to claim 6, wherein the presence or absence of a nucleotide sequence variation is determined in a 5'-noncoding region, 3'-noncoding region or intron region of SEQ ID NO:2 or its complementary sequence.

8. An isolated polynucleotide consisting of a nucleic acid sequence selected from the group consisting of
   (a) a sequence of at least 5000 contiguous nucleotides within the region consisting of the sequence of nucleotides from position 1 through position 12802 of SEQ ID NO:2,
   (b) a sequence of at least 2000 contiguous nucleotides within the region consisting of the sequence of nucleotides from position 55761 through position 58735 of SEQ ID NO:2,
   (c) a sequence of nucleotides complementary to the nucleotide sequence of (a), and
   (d) a sequence of nucleotides complementary to the nucleotide sequence of (b).

9. A composition comprising the polynucleotide of claim 8 and a carrier.

10. A kit comprising one or more polynucleotides of claim 8, optionally labeled.

11. The kit according to claim 10, wherein which further comprises the polynucleotide of clause (b) of claim 1or its complementary sequence, optionally labelled.

12. A solid support comprising one or more polynucleotides of claim 8.

13. The solid support of claim 12 wherein said support is a microarray.

14. The solid support of claim 12, wherein said solid support is a microarray, and wherein the microarray further comprises a polynucleotide of claim 1.

15. A method of detecting the presence or absence of a polynucleotide having the nucleic acid sequence set forth in SEQ ID NO:2 or its complementary sequence in a sample, said method comprising
   (a) contacting the sample with a polynucleotide of claim 8 in 50% formamide and 5×SCC at 65° C., and
   (b) determining whether the polynucleotide binds to a polynucleotide sequence in the sample,
   wherein binding of a polynucleotide of the sample to a polynucleotide of claim 6 detects the presence of a polynucleotide comprising SEQ ID NO:2.

16. An isolated polynucleotide consisting of a fragment of the polynucleotide of claim 1, said fragment consisting of an intron region of SEQ ID NO:2 selected from the group consisting of the sequence of nucleotides, between positions 18525–19411, the sequence of nucleotides between positions 19481–20985, the sequence of nucleotides between positions 21046–23146, the sequence of nucleotides between positions 23219–25408, the sequence of nucleotides between positions 25679–28128, the sequence of nucleotides between positions 28873–30372, the sequence of nucleotides between positions 32088–34184, the sequence of nucleotides between positions 34284–36002, the sequence of nucleotides between positions 36550–39674, and the sequence of nucleotides between positions 41031–55646 of SEQ ID NO:2 and nucleic acid sequence regions that are the complements thereof.

17. A composition comprising the polynucleotide of claim 16 and a carrier.

18. A kit comprising one or more polynucleotides of claim 16, optionally labeled.

19. A solid support comprising one or more polynucleotides of claim 16.

20. The solid support of claim 19 wherein said support is a microarray.

21. A method of detecting the presence or absence of a polynucleotide having the nucleic acid sequence set forth in SEQ ID NO:2 or its complementary sequence in a sample, said method comprising (a) contacting the sample with a polynucleotide of claim 15 in 50% formamide and 5×SCC at 65° C., and (b) determining whether the polynucleotide binds to a polynucleotide sequence in the sample, wherein binding of a polynucleotide of the sample to a polynucleotide of claim 16 detects the presence of a polynucleotide comprising SEQ ID NO:2.

* * * * *